US008827913B2

(12) United States Patent
Havel et al.

(10) Patent No.: US 8,827,913 B2
(45) Date of Patent: Sep. 9, 2014

(54) VERIFICATION OF PRESSURE METRICS

(75) Inventors: William J. Havel, Maple Grove, MN (US); Tommy D. Bennett, Shoreview, MN (US); Yong Kyun Cho, Maple Grove, MN (US); Robert T. Taepke, II, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 481 days.

(21) Appl. No.: 13/099,959

(22) Filed: May 3, 2011

(65) Prior Publication Data
US 2012/0283580 A1  Nov. 8, 2012

(51) Int. Cl.
| | |
|---|---|
| A61B 5/02 | (2006.01) |
| A61B 5/00 | (2006.01) |
| A61N 1/37 | (2006.01) |
| A61B 5/0215 | (2006.01) |
| A61N 1/365 | (2006.01) |

(52) U.S. Cl.
CPC ............ A61N 1/3702 (2013.01); A61B 5/7207 (2013.01); A61B 5/686 (2013.01); A61B 5/0215 (2013.01); A61B 5/7239 (2013.01); A61N 1/36564 (2013.01)
USPC .......................................... 600/485; 600/513

(58) Field of Classification Search
USPC ................................................. 600/485, 513
See application file for complete search history.

(56) References Cited

U.S. PATENT DOCUMENTS

| | | | |
|---|---|---|---|
| 5,271,392 A | 12/1993 | Ferek-Petric | |
| 5,368,040 A | 11/1994 | Carney | |
| 5,374,282 A | 12/1994 | Nichols et al. | |
| 5,423,869 A | 6/1995 | Poore et al. | |
| 5,480,412 A | 1/1996 | Mouchawar et al. | |
| 5,496,361 A | 3/1996 | Moberg et al. | |
| 5,531,772 A | 7/1996 | Prutchi | |
| 5,628,777 A | 5/1997 | Moberg et al. | |
| 5,743,267 A | 4/1998 | Nikolic et al. | |
| 5,814,089 A | 9/1998 | Stokes et al. | |
| 6,009,349 A | 12/1999 | Mouchawar et al. | |
| 6,198,968 B1 | 3/2001 | Prutchi et al. | |

(Continued)

FOREIGN PATENT DOCUMENTS

| | | |
|---|---|---|
| WO | 03057314 A1 | 7/2003 |
| WO | 2006081451 A1 | 8/2006 |

(Continued)

OTHER PUBLICATIONS

International Search Report and Written Opinion of international application No. PCT/US2012/036158, dated Sep. 25, 2012, 14 pp.

(Continued)

*Primary Examiner* — Michael Kahelin
*Assistant Examiner* — Mitchell Alter

(57) ABSTRACT

An example system may include at least one pressure sensor configured to measure a cardiovascular pressure signal and another medical device configured to measure an electrical depolarization signal of the heart. The system determines a plurality of cardiovascular pressure metrics based on the measured cardiovascular pressure signal, including at least one cardiovascular pressure metric indicative of a timing of at least one cardiac pulse. The system also determines a metric indicative of a timing of at least one heart depolarization within the measured electrical depolarization signal. The system compares the timing of the at least one cardiac pulse to the timing of the at least one depolarization, and determines whether to discard the plurality of cardiovascular pressure metrics based on whether the timings substantially agree.

10 Claims, 13 Drawing Sheets

(56) References Cited

U.S. PATENT DOCUMENTS

| | | |
|---|---|---|
| 6,491,639 B1 | 12/2002 | Turcott |
| 6,650,940 B1 | 11/2003 | Zhu et al. |
| 6,885,891 B2 | 4/2005 | Cho et al. |
| 7,035,684 B2 | 4/2006 | Lee |
| 7,130,681 B2 | 10/2006 | Gebhardt et al. |
| 7,263,399 B2 * | 8/2007 | Carlson .................. 600/509 |
| 7,367,951 B2 | 5/2008 | Bennett et al. |
| 7,708,693 B2 | 5/2010 | Bennett et al. |
| 7,742,815 B2 | 6/2010 | Salo et al. |
| 8,321,003 B2 * | 11/2012 | Zhang et al. ............. 600/513 |
| 2002/0019586 A1 | 2/2002 | Teller et al. |
| 2003/0023178 A1 | 1/2003 | Bischoff et al. |
| 2003/0083570 A1 | 5/2003 | Cho et al. |
| 2003/0105496 A1 | 6/2003 | Yu et al. |
| 2005/0113647 A1 | 5/2005 | Lee et al. |
| 2005/0119708 A1 | 6/2005 | Haefner |
| 2006/0106323 A1 | 5/2006 | Bischoff et al. |
| 2006/0167359 A1 | 7/2006 | Bennett et al. |
| 2006/0293714 A1 | 12/2006 | Salo et al. |
| 2007/0060959 A1 | 3/2007 | Salo et al. |
| 2007/0088400 A1 | 4/2007 | Jacobson |
| 2007/0239057 A1 * | 10/2007 | Pu et al. .................. 600/529 |
| 2008/0195165 A1 * | 8/2008 | Stahmann et al. ............. 607/18 |
| 2008/0243016 A1 | 10/2008 | Liao et al. |
| 2009/0048524 A1 | 2/2009 | Wildau et al. |
| 2009/0275843 A1 | 11/2009 | Karamanoglu et al. |
| 2009/0299421 A1 | 12/2009 | Sawchuk |
| 2009/0299422 A1 | 12/2009 | Ousdigian et al. |
| 2009/0299429 A1 | 12/2009 | Mayotte |
| 2009/0326600 A1 | 12/2009 | Kracker |
| 2010/0114204 A1 | 5/2010 | Burnes et al. |
| 2010/0160794 A1 * | 6/2010 | Banet et al. .................. 600/485 |
| 2010/0204592 A1 | 8/2010 | Hatib et al. |
| 2012/0123232 A1 * | 5/2012 | Najarian et al. ............. 600/345 |

FOREIGN PATENT DOCUMENTS

| | | |
|---|---|---|
| WO | 2007068284 A1 | 6/2007 |
| WO | 2009025667 A1 | 2/2009 |
| WO | 2009134585 A1 | 11/2009 |

OTHER PUBLICATIONS

Reynolds et al., "Measurement of pulmonary artery diastolic pressure from the right ventricle," Journal of the American College of Cardiology, vol. 25, No. 5, Apr. 1, 1995, pp. 1176-1182.

Jadvar et al., "Computer analysis of right ventricular pressure for improved discrimination of ventricular tachyarrhythmias," Proceedings of the Computers in Cardiology Meeting, Chicago, IL, meeting 17, Sep. 23, 1990, pp. 35-38.

Ohlsson et al., "Continuous ambulatory haemodynamic monitoring with an implantable system. The feasibility of a new technique," European Heart Journal, vol. 19, No. 1, Jan. 1998, pp. 174-184.

Yoon et al., "Automated analysis of intracardiac blood pressure waveforms for implantable defibrillators," Computers in Cardiology, vol. 25, Sep. 13, 1998, pp. 269-272.

International Preliminary Report on Patentability from International Application No. PCT/US2012/036158, dated Nov. 5, 2013, 9 pp.

Beckers et al, "ACTS: Automated Calculation of Tachograms and Systograms," Progress in Biomedical Research, Apr. 1999, pp. 160-165.

Jadvar et al., "Computer Analysis of Right Ventricular Pressure for Improved Discrimination of Ventricular Tachyarrhythmias," Proceedings of the Computer in Cardiology Meeting, Sep. 1990, 4 pp.

"#AS168—Analysis of Intraventricular Pressure Wave Data (LVP Analysis)," Biopac Development, 1996, retrieved from http://www.biopac.com/Manuals/app_pdf/app168_mp.pdf, 8 pp.

* cited by examiner

VERIFICATION OF PRESSURE METRICS

TECHNICAL FIELD

The disclosure relates to medical devices and, more particularly, to implantable medical devices that monitor cardiovascular pressure.

BACKGROUND

A variety of implantable medical devices for delivering a therapy and/or monitoring a physiological condition have been clinically implanted or proposed for clinical implantation in patients. Implantable medical devices may deliver electrical stimulation or drug therapy to, and/or monitor conditions associated with, the heart, muscle, nerve, brain, stomach or other organs or tissue, as examples. Implantable medical devices may include or be coupled to one or more physiological sensors, which may be used in conjunction with the device to monitor signals related to various physiological conditions from which a patient state or the need for a therapy can be assessed.

Some implantable medical devices may employ one or more elongated electrical leads carrying stimulation electrodes, sense electrodes, and/or other sensors. Implantable medical leads may be configured to allow electrodes or other sensors to be positioned at desired locations for delivery of stimulation or sensing. For example, electrodes or sensors may be carried at a distal portion of a lead. A proximal portion of the lead may be coupled to an implantable medical device housing, which may contain circuitry such as stimulation generation and/or sensing circuitry. Other implantable medical devices may employ one or more catheters through which the devices deliver a therapeutic fluid to a target site within a patient. Examples of such implantable medical devices include heart monitors, pacemakers, implantable cardioverter defibrillators (ICDs), myostimulators, neurostimulators, therapeutic fluid delivery devices, insulin pumps, and glucose monitors.

Pressure sensors may be employed in conjunction with implantable medical devices as physiological sensors configured to detect changes in blood pressure. Example pressure sensors that may be useful for measuring blood pressure may employ capacitive, piezoelectric, piezoresistive, electromagnetic, optical, resonant-frequency, or thermal methods of pressure transduction.

SUMMARY

In general, this disclosure describes techniques for verifying cardiovascular pressure metrics obtained by monitoring a cardiovascular pressure signal. These verification techniques may include determining a first cardiovascular pressure metric, such as a cardiac pulse interval or rate, from a cardiovascular pressure signal detected by a pressure sensor implanted within the circulatory system of a patient. The verification techniques may further include comparing the first cardiovascular pressure metric to a corresponding cardiac electrical metric, such as a cardiac depolarization interval or rate, obtained from measuring an electrical depolarization signal of the heart. In some examples, the verification techniques may include comparing the first cardiovascular pressure metric to a corresponding second cardiovascular pressure metric, such as a second pulse interval or rate, obtained by monitoring a second pressure signal.

Agreement between the pressure metric and the electrical metric, or between two pressure metrics, may provide an indicium of the reliability of one or more other cardiovascular pressure metrics determined based on a measured cardiovascular pressure signal. Using the techniques of this disclosure, a medical device may more reliably deliver drug therapy or therapeutic electrical stimulation, or acquire diagnostic information, based on various pressure metrics determined from a cardiovascular pressure signal. The techniques of this disclosure may also avoid the use of communication bandwidth and power consumption that a direct and/or continuous comparison of the raw cardiovascular pressure signal and the electrical depolarization signal of the heart may require.

In one example, a method comprises measuring, by a pressure sensor, a cardiovascular pressure signal, and determining a plurality of cardiovascular pressure metrics based on the measured cardiovascular pressure signal, wherein the plurality of cardiovascular metrics includes at least one cardiovascular pressure metric indicative of a timing of at least one cardiac pulse. The method further comprises measuring, by a medical device that is coupled to the pressure sensor, an electrical depolarization signal of the heart, and determining a metric indicative of a timing of at least one heart depolarization based on the measured electrical depolarization signal. The method further comprises comparing the timing of the at least one cardiac pulse to the timing of the at least one heart depolarization, and determining whether to discard the plurality of cardiovascular pressure metrics based on whether the timings substantially agree.

In another example, a system comprises at least one pressure sensor configured to measure a cardiovascular pressure signal, and a medical device configured to measure an electrical depolarization signal of the heart. The system further comprises at least one analysis module configured to determine a plurality of cardiovascular pressure metrics based on the measured cardiovascular pressure signal, wherein the plurality of cardiovascular metrics includes at least one cardiovascular pressure metric indicative of a timing of at least one cardiac pulse, and determine a metric indicative of a timing of at least one heart depolarization based on the measured electrical depolarization signal. The system further comprises at least one processor configured to compare the timing of the at least one cardiac pulse to the timing of the at least one heart depolarization, and determine whether to discard the plurality of cardiovascular pressure metrics based on whether the timings substantially agree.

In another example, a system comprises means for measuring a cardiovascular pressure signal, means for measuring an electrical depolarization signal of the heart, means for determining a plurality of cardiovascular pressure metrics based on the measured cardiovascular pressure signal, wherein the plurality of cardiovascular metrics includes at least one cardiovascular pressure metric indicative of a timing of at least one cardiac pulse, means for determining a metric indicative of a timing of at least one heart depolarization within the measured electrical depolarization signal, means for comparing the timing of the at least one cardiac pulse to the timing of the at least one depolarization signal, and means for determining whether to discard the plurality of cardiovascular pressure metrics based on whether the timings substantially agree.

In another example, a method comprises measuring, by a first pressure sensor, a first cardiovascular pressure signal, and determining a plurality of first cardiovascular pressure metrics based on the measured first cardiovascular pressure signal, wherein the plurality of first cardiovascular metrics includes at least one first cardiovascular pressure metric indicative of a timing of at least one cardiac pulse. The method further comprises measuring, by a second pressure sensor that is coupled to the first pressure sensor, a second cardiovascular pressure signal, and determining at least one second cardiovascular pressure metric based on the measured second cardiovascular pressure signal, wherein the at least one second cardiovascular pressure metric is indicative of a timing of at least one cardiac pulse. The method further comprises comparing the timing of the at least one cardiac pulse indicated by the first cardiovascular pressure metric to the timing of the at least one cardiac pulse indicated by the second cardiovascular pressure metric, and determining whether to discard the plurality of first cardiovascular pressure metrics based on whether the timings substantially agree.

In another example, a system comprises a first pressure sensor configured to measure a first cardiovascular pressure signal, a second pressure sensor configured to measure a second cardiovascular pressure signal, wherein the first and second pressure sensors communicate with each other, and one or more analysis modules implemented in one or more of the first and second pressure sensors. The one or more analysis modules are configured to determine a plurality of first cardiovascular pressure metrics based on the measured first cardiovascular pressure signal, wherein the plurality of first cardiovascular metrics includes at least one first cardiovascular pressure metric indicative of a timing of at least one cardiac pulse, determine at least one second cardiovascular pressure metric based on the measured second cardiovascular pressure signal, wherein the at least one second cardiovascular pressure metric is indicative of a timing of at least one cardiac pulse, compare the timing of the at least one cardiac pulse indicated by the first cardiovascular pressure metric to the timing of the at least one cardiac pulse indicated by the second cardiovascular pressure metric, and determine whether to discard the plurality of first cardiovascular pressure metrics based on whether the timings substantially agree.

In another example, a method comprises measuring, by a medical device that is coupled to a pressure sensor, an electrical depolarization signal of the heart, detecting asystole based on the electrical depolarization signal of the heart, and, in response to the detection of asystole, directing the pressure sensor to measure a cardiovascular pressure signal.

In another example, a system comprises a pressure sensor and a medical device. The medical device is configured to measure an electrical depolarization signal of the heart, detect asystole based on the electrical depolarization signal of the heart, and in response to the detection of asystole, directing the pressure sensor to measure a cardiovascular pressure signal.

The details of one or more aspects of the disclosure are set forth in the accompanying drawings and the description below. Other features, objects, and advantages will be apparent from the description and drawings, and from the claims.

DETAILED DESCRIPTION

This disclosure describes various techniques for verifying cardiovascular pressure metrics obtained through cardiovascular pressure monitoring. Heart rate is often measured by sensing ventricular electrical depolarizations from an electrocardiogram (ECG) or intracardiac electrogram (EGM). Sensing the electrical activity of the heart may be performed by IMDs or external monitoring devices. Thus, although in many of the examples described herein sensing of electrical activity of the heart is done by an IMD, in other examples an external medical device may sense electrical activity of the heart and perform the various techniques described herein with respect to an IMD. Pulse rate and other cardiovascular pressure metrics, such as systolic pressure and diastolic pressure, may be derived from a cardiovascular pressure signal from one or more pressure sensors in the pulmonary artery, aorta, atria, ventricle, or other locations within the cardiovascular system. The measured cardiovascular pressure may be subject to interference from pressure fluctuations due, for example, to respiration, wave reflection, motion, and coughing. Using the techniques of this disclosure, the cardiovascular pressure metrics determined from the cardiovascular pressure signal may be verified by a comparison with a cardiac electrical metric, such as a heart rate, obtained from a measured electrical depolarization signal.

Figure 1A:
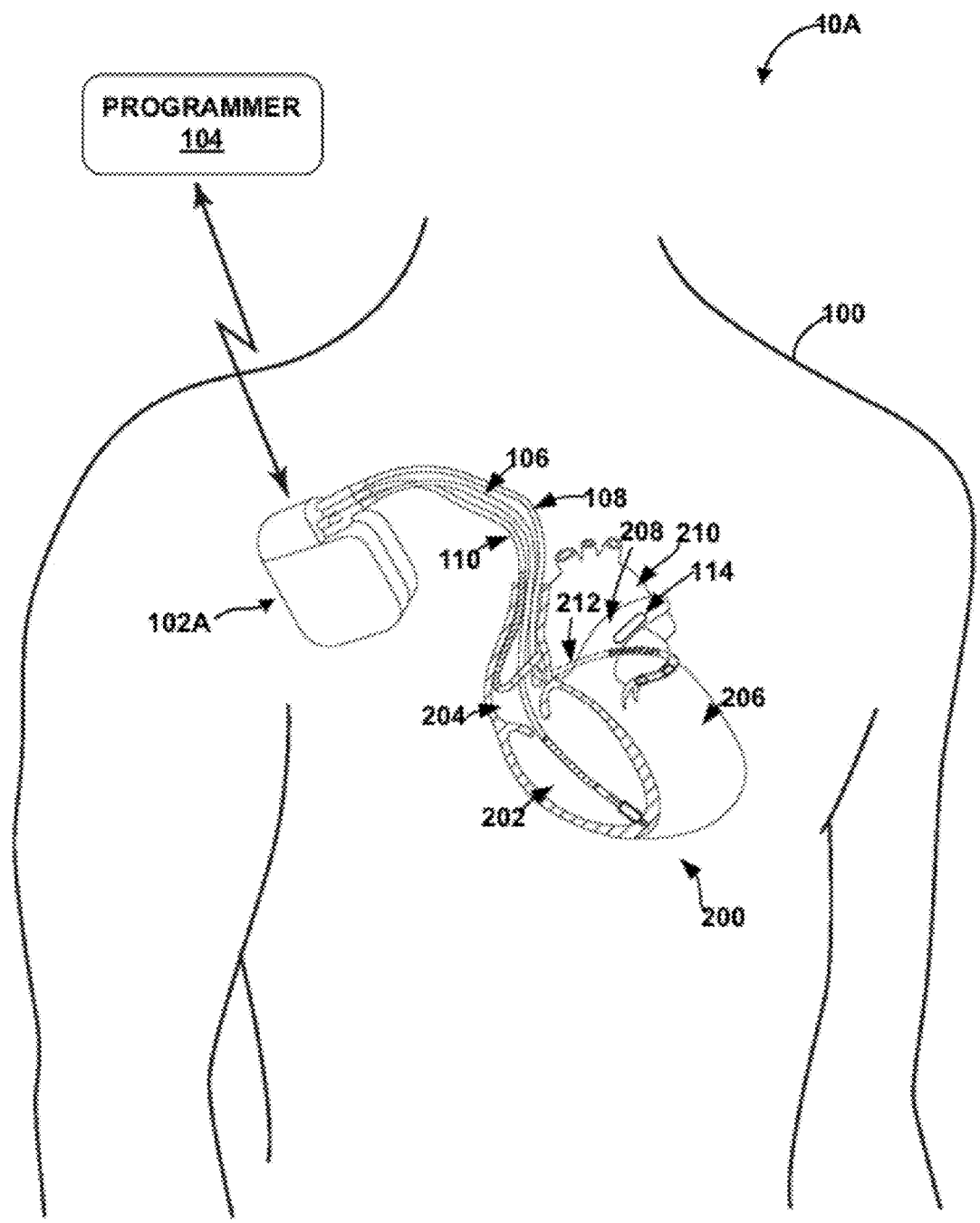
FIGS. 1A and 1B are conceptual diagrams illustrating example systems that may be used to provide therapy to and/or monitor a heart of a patient.

FIG. 1A is a conceptual diagram illustrating an example system 10A that may be used to monitor and/or provide therapy to heart 200 of patient 100. Patient 100 will ordinarily, but not necessarily, be a human. System 10 includes IMD 102A (generically "IMD 102"), which is coupled to leads 106, 108, and 110, and programmer 104. IMD 102A may be, for example, an implantable pacemaker, cardioverter, and/or defibrillator that senses electrical signals of heart 200, and provides electrical signals to heart 200, via electrodes coupled to one or more of leads 106, 108, and 110. In accordance with certain techniques of this disclosure, IMD 102A may receive pressure information from a pressure sensor 114 located within, for example, pulmonary artery 208 of patient 100 and, in some examples, provide therapeutic electrical signals to heart 200 based on the received pressure information. Pressure sensor 114 may be coupled to IMD 102 via a lead, or wirelessly. In some examples, IMD 102A may control pressure sensor 114 to make one or more pressure measurements in response to the detection of an arrhythmia in the heart of patient 100. The pressure measurements performed by pressure sensor 114 may be used to verify the arrhythmia or refine the diagnosis or treatment of the condition by IMD 102B.

Leads 106, 108, 110 extend into the heart 200 of patient 100 to sense electrical activity of heart 200 and/or deliver electrical stimulation to heart 200. In the example shown in FIG. 1A, right ventricular lead 106 extends through one or more veins (not shown), the superior vena cava (not shown), and right atrium 204, and into right ventricle 202. Left ventricular coronary sinus lead 108 extends through one or more veins, the vena cava, right atrium 204, and into the coronary sinus 212 to a region adjacent to the free wall of left ventricle 206 of heart 200. Right atrial lead 110 extends through one or more veins and the vena cava, and into the right atrium 204 of heart 200.

IMD 102A may sense electrical signals attendant to the depolarization and repolarization of heart 200 via electrodes (not shown in FIG. 1A) coupled to, for example, at least one of the leads 106, 108, 110. In some examples, IMD 102A provides pacing pulses to heart 200 based on the electrical signals sensed within heart 200. The configurations of electrodes used by IMD 102A for sensing and pacing may be unipolar or bipolar. IMD 102A may also provide defibrillation therapy and/or cardioversion therapy via electrodes located on at least one of the leads 106, 108, 110. IMD 102A may detect arrhythmia of heart 200, such as fibrillation of ventricles 202 and 206, and deliver defibrillation therapy to heart 200 in the form of electrical pulses. In some examples, IMD 102A may be programmed to deliver a progression of therapies, e.g., pulses with increasing energy levels, until a fibrillation of heart 200 is stopped. IMD 102A detects fibrillation by employing one or more fibrillation detection techniques known in the art. The number and configuration of electrodes and leads is merely an example and IMD 102A may be coupled to more or fewer electrodes and leads. In some configurations, IMD 102A may include an integral or housing electrode, which may facilitate unipolar delivery of electrical signals or sensing via a combination of one or more of the electrodes on the leads and the housing electrode.

In some examples, programmer 104 may be a handheld computing device or a computer workstation. A user, such as a physician, technician, or other clinician, may interact with programmer 104 to communicate with IMD 102A. For example, the user may interact with programmer 104 to retrieve physiological or diagnostic information from IMD 102A. A user may also interact with programmer 104 to program IMD 102A, e.g., select values for operational parameters of the IMD.

For example, the user may use programmer 104 to retrieve information from IMD 102A regarding the rhythm of heart 200, trends therein over time, or arrhythmic episodes. As another example, the user may use programmer 104 to retrieve information from IMD 102A regarding other sensed physiological parameters of patient 100, such as intracardiac or intravascular pressure, activity, posture, respiration, or thoracic impedance. As another example, the user may use programmer 104 to retrieve information from IMD 102A regarding the performance or integrity of IMD 102A or other components of system 10A, such as leads 106, 108 and 110, pressure sensor 114, or a power source of IMD 102A. The user may use programmer 104 to program a therapy progression, select electrodes used to deliver defibrillation pulses, select waveforms for the defibrillation pulse, or select or configure a fibrillation detection algorithm for IMD 102A. The user may also use programmer 104 to program aspects of other therapies provided by IMD 102A, such as cardioversion or pacing therapies.

IMD 102A and programmer 104 may communicate via wireless communication using any technique known in the art. Examples of communication techniques may include, for example, low frequency or radiofrequency (RF) telemetry, but other techniques are also contemplated. In some examples, programmer 104 may include a programming head that may be placed proximate to the patient's body near the IMD 102A implant site in order to improve the quality or security of communication between IMD 102A and programmer 104.

Figure 1B:
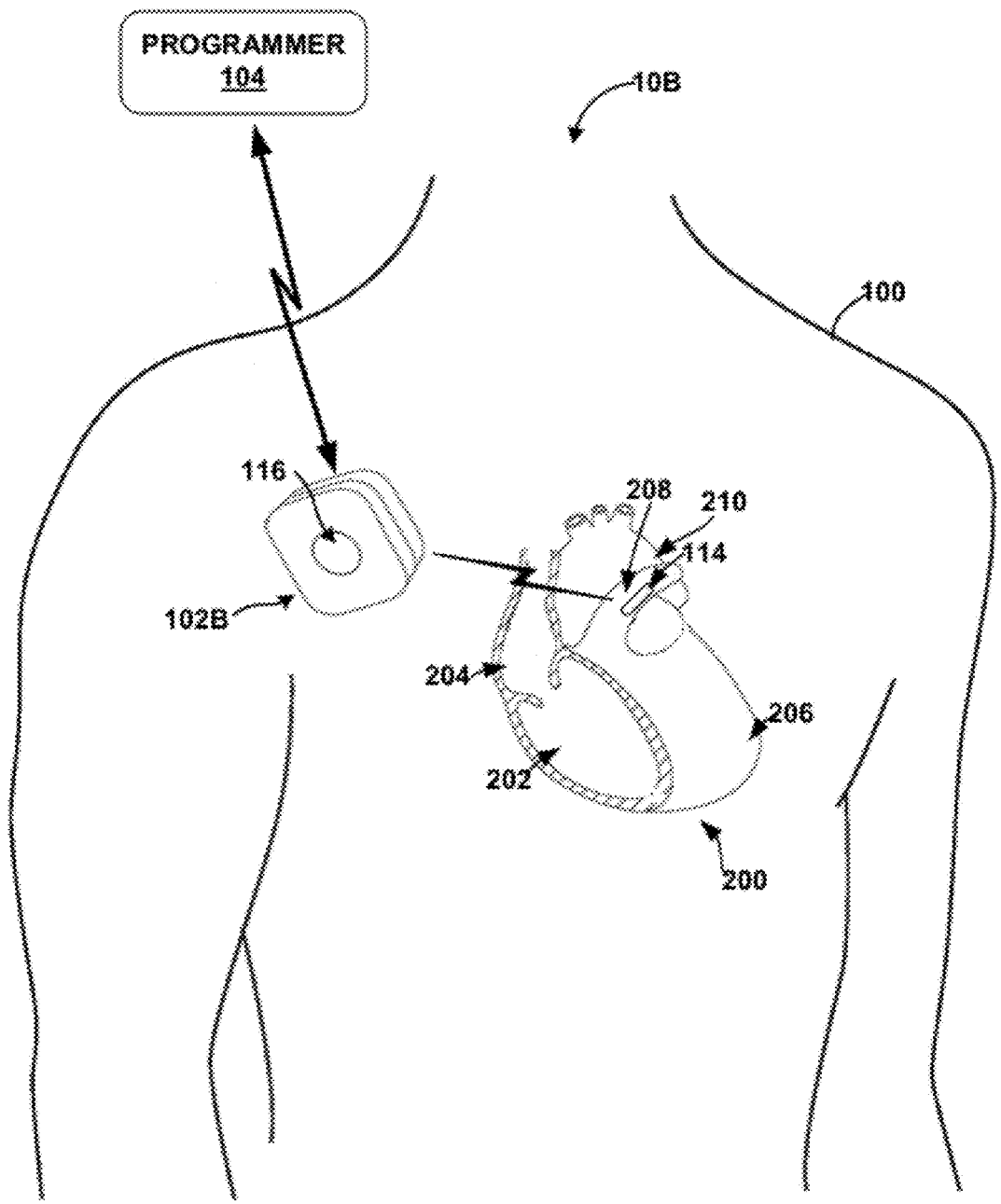

FIG. 1B is a conceptual diagram illustrating another example system 10B that may be used to monitor and/or provide therapy to heart 200 of patient 100. System includes IMD 102B (generically 'IMD 102') with integral electrodes 116 and 118, e.g. housing electrodes, programmer 104, and a pressure sensor 114. In some configurations, IMD 102B may have two or more housing electrodes. IMD 102B may be, for example, an implantable monitor that monitors electrical signals of heart 200, e.g., senses electrical signals attendant to the depolarization and repolarization of heart 200, via electrodes 116.

IMD 102B may include additional sensors, such as an accelerometer for monitoring patient posture or activity. In some examples, IMD 102B may be implemented in, or similar to, a Reveal® implantable monitor, available from Medtronic, Inc. of Minneapolis, Minn. In other examples, IMD 102B may be configured to provide a therapy, such as providing therapeutic electrical stimulation via electrodes 116 or 118. In some examples, IMD 102B may implanted proximate to or within target tissue for the therapy, such as within a chamber of the heart to which IMD 102B may deliver cardiac pacing.

In accordance with certain techniques of this disclosure, IMD 102B may wirelessly receive pressure information from pressure sensor 114 located within, for example, pulmonary artery 208 of patient 100. In some examples, IMD 102B may store the pressure information and/or relay the pressure information to another device, e.g., programmer 104. In some examples, IMD 102B may diagnose a patient condition based, at least in part, on pressure information received from pressure sensor. In some examples, IMD 102B may provide therapeutic electrical signals to heart 200 based on the received pressure information. In further examples, IMD 102B may control pressure sensor 114 to take one or more pressure measurements in response to the detection of an arrhythmia in the heart of patient 100. The pressure measurements performed by pressure sensor 114 may be used to verify the arrhythmia or refine the diagnosis or treatment of the condition by IMD 102B.

Figure 2:
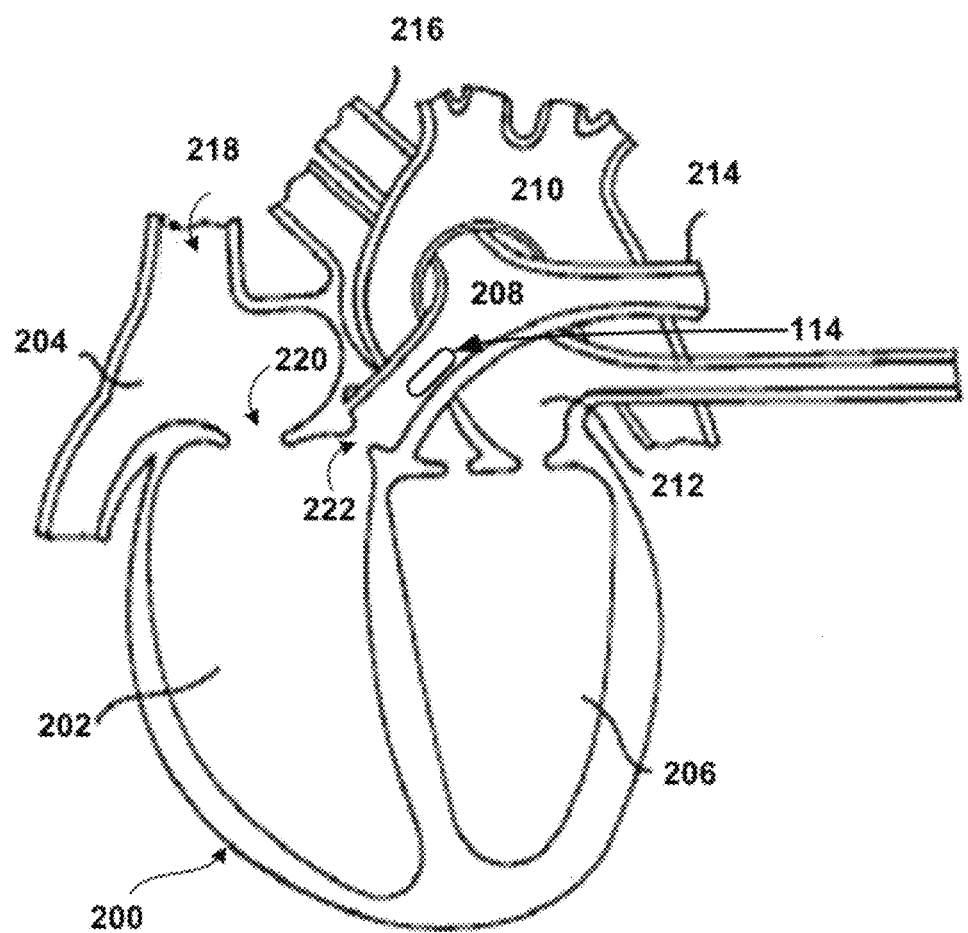
FIG. 2 is a conceptual diagram of a human heart, including an example pressure sensor.

As shown in FIG. 2, pressure sensor 114 may be a leadless assembly, e.g., need not be physically coupled to an IMD or other device via a lead, and need not otherwise be coupled to any leads. Although not depicted, pressure sensor 114 may include wireless communication capabilities such as low frequency or radiofrequency (RF) telemetry, or other wireless communication techniques that allow sensor 114 to communicate with IMD 102B, programmer 104, or another device. Pressure sensor 114 may be located in the pulmonary artery 208, right ventricle 202, aorta, and other locations within the pulmonary and systemic circulatory systems of patient 100. Pressure sensor 115 may be affixed to the wall of the pulmonary artery 208 or, as another example, the wall of the right ventricle 202, using any number of well-known techniques. For example, pressure sensor 208 may include fixation elements, e.g., helical tines, hooked tines, barbs, or the like, that allow sensor 114 to be secured to tissue at a desired location. In other examples, pressure sensor 114 may be attached to a stent having any variety of conformations, for example, and the stent/sensor combination may be implanted within pulmonary artery 208.

Pressure sensor 114 may be implanted within pulmonary artery 208 or in other locations within the pulmonary or systemic circulatory systems of patient 100 by, for example, using a delivery catheter. For example, a physician may deliver pressure sensor(s) 114 via a delivery catheter, transvenously through either the internal jugular or femoral veins. The delivery catheter then extends through superior vena cava 218, right atrioventricular valve 220, right ventricle 202, and pulmonary valve 222 into pulmonary artery 208. In other examples, pressure sensor 114 may be implanted after a physician has opened the chest of the patient by cutting through the sternum, or via an open-heart procedure, which may be similar to a valve replacement surgery.

Pressure sensor 114 generates a pressure signal as a function of the fluid pressure in, for example, pulmonary artery 208. An IMD 102, programmer 104, and/or another device, e.g., external monitoring equipment, may receive a cardiac cycle length (or pulse rate or pulse-to-pulse intervals) and/or other cardiovascular pressure metrics transmitted by pressure sensor 114. In other examples, pressure sensor 114 may receive cardiac depolarization data or other electrical metrics from an IMD 102 for comparison purposes.

More generally, the techniques for verifying cardiovascular pressure metrics described herein may be implemented in an IMD 102, pressure sensor 114, programmer 24, another computing device, such as a remote server, or any combination of such devices. In some example implementations, one or more pressure sensors 114 may communicate a cardiovascular pressure signal to another device, e.g., IMD 102, which may determine one or more cardiovascular pressure metrics based on the signal. In other examples, one or more pressure sensors 114 may determine cardiovascular pressure metrics based on the signal, and transmit the pressure metrics to one or more other devices, e.g., IMD 102. In some examples, IMD 102 may compare a cardiovascular pressure metric to a corresponding cardiac electrical metric for verification of one or more other cardiovascular pressure metrics. In other examples, pressure sensor 114 or another device may receive the electrical metric from IMD 102 for comparison to the corresponding cardiovascular pressure metric and verification of other cardiovascular pressure metrics. In a further example, as will be described in greater detail below, one or more pressure sensors 114 may compare and verify cardiovascular pressure metrics received from one or more other pressure sensors 114.

Figure 3:
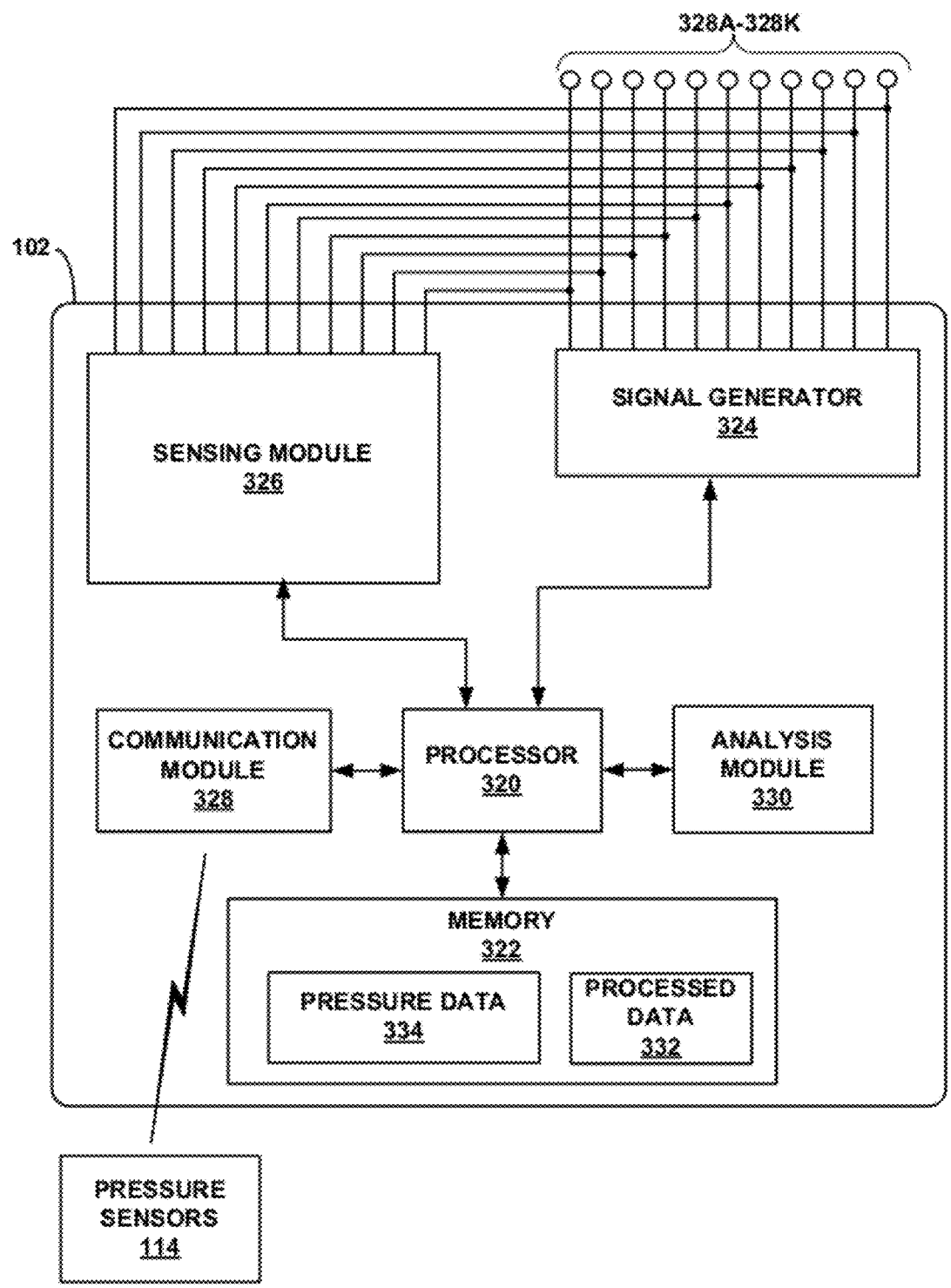
FIG. 3 is a functional block diagram illustrating an example configuration of an IMD that may be used to implement certain techniques of this disclosure.

FIG. 3 is a functional block diagram illustrating an example configuration of an IMD 102 that may be used to implement certain techniques of this disclosure. In the illustrated example, IMD 102A includes a processor 320, memory 322, signal generator 324, sensing module 326, communication module 328, and pressure analysis module 330. As seen in FIG. 3, one or more pressure sensors 114 may be in communication with IMD 102 via communication module 328. In the illustrated example, IMD 102 is coupled to electrodes 328A-328K ("electrodes 328"), which may correspond to the electrodes on leads 106, 108 and 110 coupled to IMD 102A (FIG. 1A) and an integral electrode on the housing of IMD 102A, or to integral electrodes, e.g., electrodes 116 and 118 (FIG. 1B), as shown with IMD 102B in FIG. 1B. IMD 102 may, in some examples, be coupled to more or fewer electrodes 328.

In some examples, analysis module 330 analyzes the cardiovascular pressure signal or metrics received from pressure sensor(s) 114. Analysis module 330 may be implemented as software, firmware, hardware, or any combination thereof. In some example implementations, analysis module 330 may be a software process implemented in or executed by processor 320. Memory 322 is one example of a non-transitory, computer-readable storage medium that includes computer-readable instructions that, when executed by processor 320, cause IMD 102 and processor 320 to perform various functions attributed to IMD 102 and processor 320 in this disclosure. Memory 322 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

In some example implementations, processor 320 of IMD 102 may control signal generator 324 to deliver stimulation therapy to heart 200 based on the determined cardiac cycle length or various cardiovascular pressure metrics. For example, upon receiving a systolic pressure from pressure sensor 114, analysis module 330 may determine that the systolic pressure in the pulmonary artery is below a predetermined threshold value. In response, processor 320 may, for example, control signal generator 324 to deliver pacing pulses to heart 200 to increase the amount of blood flow. Processor 320 may also adjust pacing settings in response to the determination. For example, processor 320 may adjust one or more atrioventricular or interventricular delays for pacing therapy, e.g., cardiac resynchronization therapy. In some examples, a clinician or an external or implantable medical device may deliver a drug or other therapy based on the determined cardiac cycle length and/or various cardiovascular pressure metrics.

Processor 320 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 320 in this disclosure may be embodied as software, firmware, hardware or any combination thereof.

In some examples, processor 320 controls signal generator 324 to deliver stimulation therapy to heart 200 according to a selected one or more of therapy programs, which may be stored in memory 322. For example, processor 320 may control signal generator 324 to deliver electrical pulses with the amplitudes, pulse widths, frequency, or electrode polarities specified by the selected one or more therapy programs.

Signal generator 324 may be electrically coupled to electrodes 328, e.g., via conductors of, for example, the respective leads 106, 108, 110 of FIG. 1A, or, in the case of integral electrodes such as integral electrodes 116 and 118, via an electrical conductor disposed within housing of IMD 102. In some examples, signal generator 324 is configured to generate and deliver electrical stimulation therapy to heart 200. In some examples, signal generator 324 delivers pacing, cardioversion, or defibrillation stimulation in the form of electrical pulses. In other examples, signal generator 324 may deliver one or more of these types of stimulation in the form of other signals, such as sine waves, square waves, or other substantially continuous time signals, or one or more specified duration bursts of such continuous signals.

Signal generator 324 may include a switch module, and processor 320 may use the switch module to select which of the available electrodes are used to deliver such stimulation. The switch module may include a switch array, switch matrix, multiplexer, or any other type of switching device suitable to selectively couple stimulation energy to selected electrodes.

In some examples, sensing module 326 monitors signals from at least one of electrodes 328 in order to monitor electrical activity of heart 200. Sensing module 326 may also include a switch module. In some examples, processor 320 may select the electrodes that function as sense electrodes via the switch module within sensing module 326.

Sensing module 326 may include one or more detection channels (not shown), each of which may comprise an amplifier. The detection channels may be used to sense the cardiac signals. Some detection channels may detect cardiac events, such as R- or P-waves, and provide indications of the occurrences of such events to processor 320. One or more other detection channels may provide the signals to an analog-to-digital converter, for processing or analysis by analysis module 330. In some examples, analysis module 330 may store the digitized versions of signals from one or more selected detection channels in memory 322 as EGM signals. In response to the signals from processor 320, the switch module within sensing module 326 may couple selected electrodes to selected detection channels, e.g., for detecting events or acquiring an EGM in a particular chamber of heart 200.

In some cases, it may be desirable for IMD 102 or other devices to have cardiovascular pressure metrics for patient 100. However, due to constraints regarding the size or location of devices, it may be not desired to have a pressure sensor included as part of IMD 102 or coupled to IMD 102 via a lead. Accordingly, cardiovascular pressure metrics such as peak-systolic pressure and end-diastolic pressure may be derived from the cardiovascular pressure from one or more wireless pressure sensors 114 in the pulmonary artery or other locations in the patient's circulatory system.

As illustrated in FIG. 3, in addition to program instructions, memory 322 may store a cardiovascular metric or other data, e.g., cardiovascular signals, received from pressure sensor 114 via communication module 328. Raw data, such as a cardiovascular pressure signal may be stored in memory 322 as pressure data 334 to be processed by analysis module 330. Processor 320 may store cardiovascular metrics processed by analysis module 330, or by pressure sensors 114, in memory 322 as processed data 332. Processed data 332 may represent metrics such as cycle lengths, pulse rates, peak-systolic pressure, end-diastolic pressure, averages or trends therein over time, or other signal morphology information determined from both the cardiovascular pressure signals. For example, processed data 332 may include cycle length data, systolic pressure data, and diastolic pressure data as processed and/or determined by analysis module 330. In addition, in some example implementations, processor 320 may order pressure sensor 114 to measure a pressure within the cardiovascular system of a patient. For example, based on predetermined timing data stored in memory 322, or timing data transmitted via a programmer, e.g., programmer 104, processor 320 may transmit, via communication module 328, instructions to pressure sensor 114 to take one or more pressure measurements.

Figure 4:
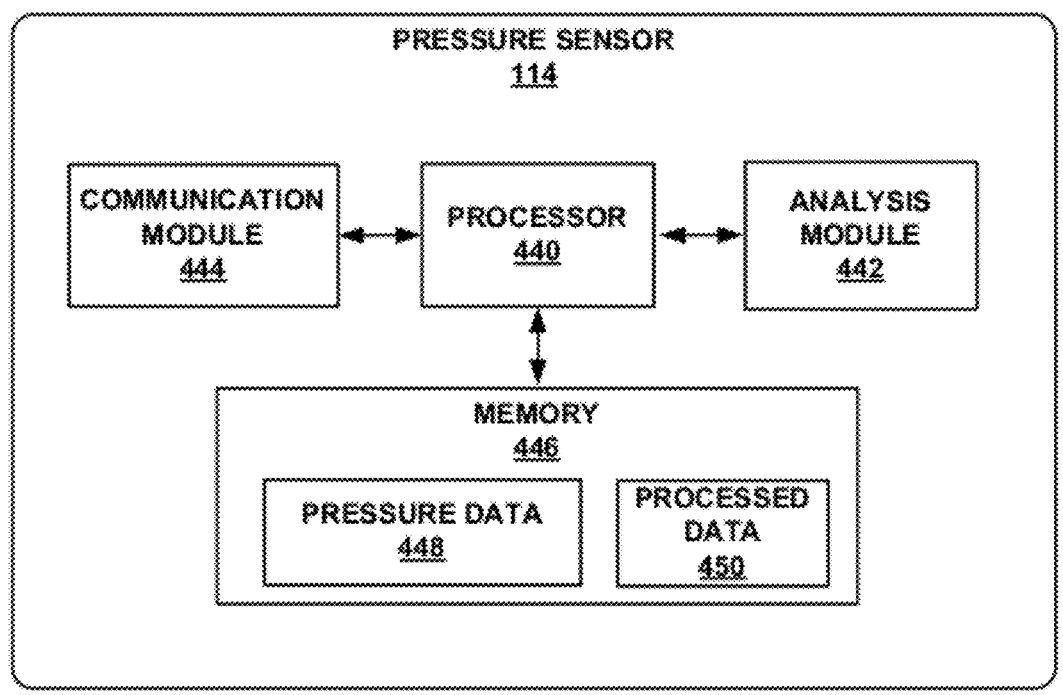
FIG. 4 is a functional block diagram illustrating an example configuration of a pressure sensor that may be used to implement certain techniques of this disclosure.

FIG. 4 is a functional block diagram illustrating an example configuration of a pressure sensor that may be used to implement certain techniques of this disclosure. In the illustrated example, pressure sensor 114 includes a processor 440, analysis module 442, communication module 444, and memory 446. Processor 440 and communication module 444 may be similar to processor 320 and communication module 328 of FIG. 3. Processor 440 may store pressure information as pressure data 448 and processed data 450 in memory 446. Pressure data 448 may include raw, unprocessed pressure information that represents a pressure signal within a pulmonary artery of a patient. Cardiovascular pressure metrics obtained by processing the cardiovascular pressure signal may be stored as processed data 450 in memory 446. In some examples, communication module 444 may transmit processed data 450 to IMD 102. In other examples, communication module 444 may transmit pressure data 448 or processed data 450 to programmer 104, or to another external device, e.g., for further analysis.

In some examples, analysis module 442 may process a cardiovascular pressure signal sensed by pressure sensor 114 and store the processed information in memory 446 as processed data 450. Analysis module 442 may be implemented as software, firmware, hardware or any combination thereof. In some example implementations, analysis module 442 may be a software process implemented in or executed by processor 440. Processed data 450 may represent the cardiovascular metrics determined based on pressure data 448, such as cycle lengths, averages, trends over time. In particular, processed data 450 may include cycle length data, cardiac pulse rate, systolic pressure, diastolic pressure, or other signal morphology information as processed and/or determined by analysis module 442. Communication module 444 may transmit processed data 442 to IMD 102, programmer 104, or another external device for further analysis.

In some examples, processor 320 of IMD 102 or processor 440 of pressure sensor 114 may compare a detected cardiac pulse interval or pulse rate measured via pressure sensor 114 to a cardiac depolarization interval or rate of heart 200 measured via an electrodes 328 connected to IMD 102. Comparing the cardiac depolarization timing to the cardiac pulse timing in this manner allows for a verification of the cardiovascular metrics obtained by analyzing the cardiovascular pressure signal.

Comparing depolarization and pulse rates or intervals in this manner may save communication bandwidth and power by allowing for the verification of cardiovascular metrics obtained for a particular time span. The comparison of these metrics enables either processor 440 aboard pressure sensor 114 or processor 320 aboard IMD 102 to determine if the cardiovascular pressure metrics are valid. If the detected cardiac pulse (or pulse rate) and the detected electric depolarization (or heart rate) do not agree, then the cardiovascular pressure signal may be experiencing noise and the resulting metrics may be discarded and the cardiovascular pressure signal re-measured.

Figure 5:
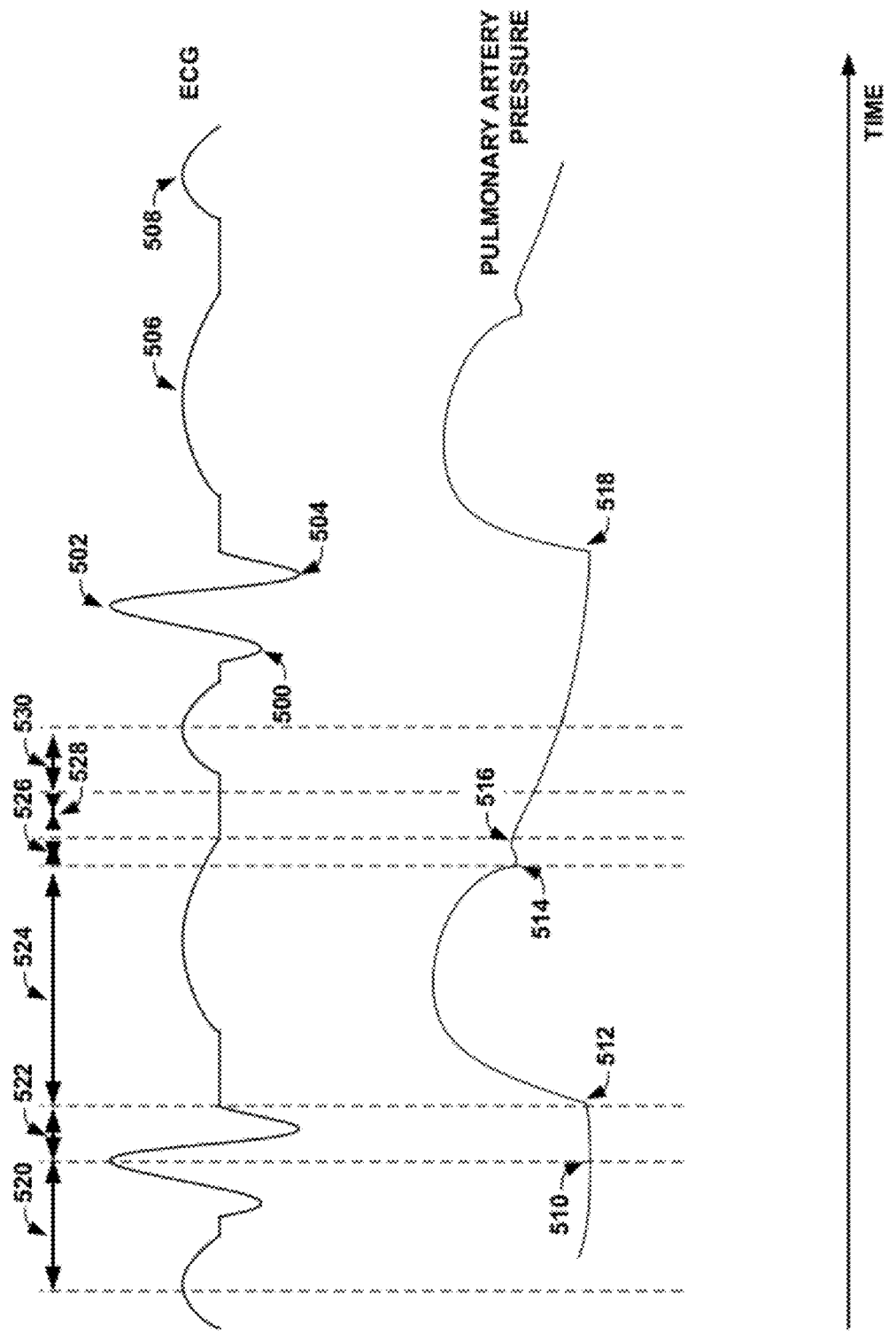
FIG. 5 is a timing diagram showing a conceptual signal indicative of pulmonary arterial pressure (PAP), and a conceptual cardiac electrogram signal, e.g., ECG, signal for the same period.

FIG. 5 is a timing diagram showing a conceptual signal indicative of pulmonary arterial pressure (PAP), and a conceptual cardiac electrogram signal for the same period. Two complete cardiac cycles are shown in both tracings. The cardiac electrogram shows electrical activity of the heart over time. Characteristics of the cardiac electrogram and PAP signal correspond to a series of discrete events in the cardiac cycle. For ease of illustration, the electrogram and PAP signal are conceptual, and include signal features, some or all of which may be present in discernable in actual signals detected by devices, e.g., an IMD and pressure sensor, described herein. Although the example of FIG. 5 illustrates and describes a PAP signal, in other examples a signal indicative of pressure in another portion of the cardiovascular system, e.g., a ventricle or aorta, may be sensed by an appropriately positioned pressure sensor.

For example, the cardiac electrogram includes five characteristic waves: Q-wave 500, R-wave 502, S-wave 504, T-wave 506, and P-wave 508, some or all of which may be detectable in a cardiac electrogram signal sensed by an IMD or external medical device. At point 510 on the PAP signal the atrioventricular valves close, blocking fluid communication between the atrium and ventricle of the heart. At point 512 the pulmonic valve (or aortic valve if the pressure sensor is disposed on the aorta) opens, allowing blood to be ejected from the heart, and at point 514 the pulmonic valve closes again. At point 516 the atrioventricular valves open while the heart muscles begin to relax. Point 518 marks the opening of the pulmonic valve and the start of another ejection period in the cardiac cycle.

Period 520, stretching from the peak of a P-wave to the peak of the subsequent R-wave, corresponds to the atrial systole, the contraction of the atria that drives blood from the atria into the ventricles. Period 522, from the peak of the R-wave to the opening of the pulmonic valves, marks a period of isovolumic contraction. The atrioventricular and pulmonic valves are closed, preventing blood flow and leading to an increase in pressure in the ventricles, but that has not yet exceeded the back-pressure in the pulmonary artery. Period 524, bounded by the opening and closing of the pulmonic valve is the ejection period of the cardiac cycle. During ejection period 524 the ventricles contract and empty of blood, driving the blood into the cardiovascular system. As the contraction of the ventricles completes, the pressure of the blood within the cardiovascular system closes the pulmonic valve 514. Period 526, bounded by the closing of the pulmonic valve 514 and the opening of the atrioventricular valves 516, is the isovolumic relaxation of the ventricles. Periods 528 and 530 are collectively known as the late diastole, where the whole heart relaxes and the atria fill with blood. Period 528 corresponds to a rapid inflow of blood while period 530 corresponds to diastasis, the period of slower flow blood into the atria before the atrial systole 520 occurs again.

IMD 102 may determine a cardiac depolarization interval or rate through any of the techniques known in the art. For example, IMD 102 may detect an electric depolarization by monitoring the electronic depolarization signal via ECG and determining when the signal crosses a set threshold corresponding to the detection of an R-wave. A cardiac depolarization interval or rate may be determined, for example, by measuring the time period between the peaks of one or more R-waves. Such rate measurement may also be achieved by thresholding the $1^{st}$ derivative of the cardiac electrogram, or according to any other technique known in the art.

Pressure sensor 114 may determine a cardiovascular pressure metric through any of the techniques known in the art. For example, pressure sensor 114 may use pressure analysis module 442 to calculate the first derivative of the PAP signal. The maximum value of the first derivative of the PAP signal for a given cardiac cycle can be used to define the beginning of a window of time and determine the systolic pressure of the patient via the maximum pressure within the pulmonary artery in the window. The pressure sensor may, for example, determine the occurrence of a cardiac pulse by monitoring the first derivative of the PAP signal for the sudden spike in pressure, or monitor the second derivative of the PAP signal for a zero-crossing, corresponding to the beginning of the expulsion period 524. A cardiac pulse rate may be determined by measuring the time period between one or more such spikes or zero-crossings.

Figure 6:
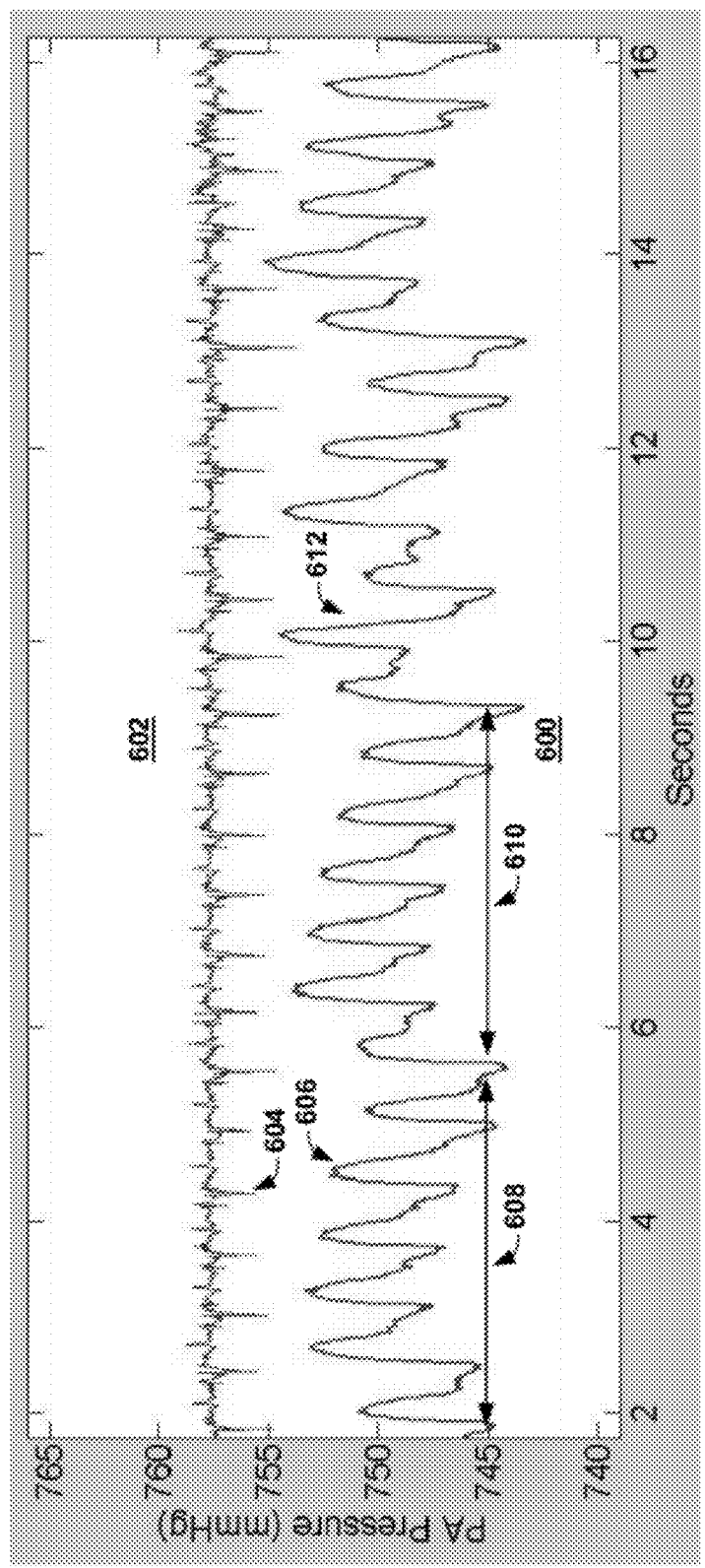
FIG. 6 is a timing diagram showing a signal indicative of pulmonary arterial pressure, and an ECG for the same period, in accordance with certain techniques of this disclosure.

FIG. 6 is a timing diagram showing a signal indicative of pulmonary arterial pressure, and an ECG for the same period. The tracings in FIG. 6 represent data taken during the testing of an implanted pressure sensor. Pressure signal tracing 600 represents the measured pulmonary artery pressure in mmHg over a span of 14 seconds. ECG tracing 602 represents the measured electrical depolarization signal for the test subject over the same period.

A comparison of pressure signal tracing 600 and ECG tracing 602 demonstrates the connection between the two tracings. For example, the R-wave in ECG tracing 602, e.g., R-wave 604, immediately precedes the sharp increase in pressure corresponding to the beginning of the expulsion phase in pressure signal tracing 600, for example expulsion 606. Each cardiac pulse shown in pressure signal tracing 600 has a corresponding R-wave spike in ECG tracing 602.

Pressure signal tracing 600 shows a pulse rate of approximately 98 beats per minute, determined by counting the number of expulsion peaks within the sample time range. Pressure signal tracing 600 also shows some evidence of mechanical noise. For example, pressure signal tracing 600 shows a periodic underlying pattern, represented in periods 608 and 610. The rise and fall of the maximum pressure in these cycles is repeated in the remainder of the tracing and may be due to a repetitive activity such as a respiratory component. The drop in pulmonary artery pressure at point 612 may be due to a movement or other physical artifact. Rapid movement or other external factors may produce sufficient disturbance to distort the measured pressure, possibly resulting in additional detected or hidden pulses.

Figure 7:
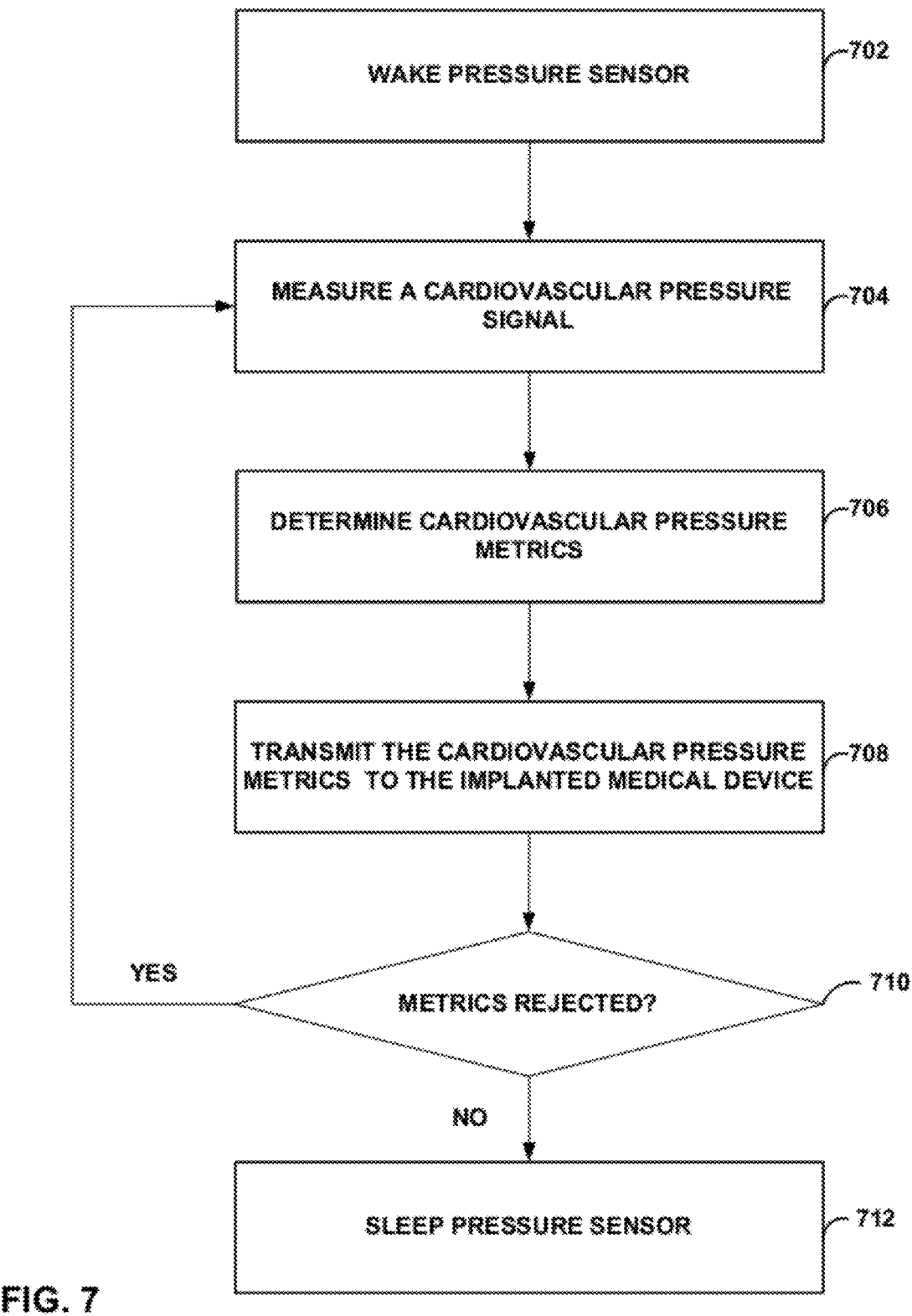
FIG. 7 is a flow diagram illustrating an example method for operating a pressure sensor coupled with an implantable medical device (IMD), in accordance with various techniques of this disclosure.

FIG. 7 is a flow diagram illustrating an example method for operating a wireless pressure sensor coupled with an implantable medical device, in accordance with various techniques of this disclosure. Although the example of FIG. 7 is described in the context of an implantable medical device coupled to the pressure sensor, in other examples the medical device may be external to the patient.

According to the example method, the pressure sensor wakes from a reduced power consumption state to perform measurements (702). The pressure sensor measures a cardiovascular pressure signal (704). The pressure sensor determines a plurality of cardiovascular metrics based on the measured cardiovascular pressure signal, including at least one metric related to the timing of at least one cardiovascular pulse, e.g., a pulse rate or interval (706). The pressure sensor transmits at least the cardiovascular pressure metric indicative of the timing of the cardiovascular pulse to the implanted medical device (708). The pressure sensor then determines whether the cardiovascular pressure metrics have been, or should be rejected, e.g., based on an indication from the implantable medical device (710). The determination of whether the cardiovascular pressure metrics should be rejected is based on a comparison of the at least on cardiovascular pressure metric indicative of pulse timing to corresponding cardiac depolarization timing. If the cardiovascular pressure metrics are rejected, the pressure sensor may discard the cardiovascular pressure metrics, and re-measures the cardiovascular pressure signal (704) and re-determines the cardiovascular pressure metrics (706). If the cardiovascular pressure metrics are not rejected, the pressure sensor returns to a reduced power consumption sleep state (712).

In some examples, the pressure sensor, e.g. pressure sensor 114, may spend some or most of its life span in a reduced power consumption sleep or hibernating state. This allows the pressure sensor to maximize its battery life. The pressure sensor may wake from the sleep state (702). Waking may occur automatically on a fixed schedule, e.g. at certain times of the day, or in response to an external command, e.g. from linked IMD 102. Such a wake command may occur over a wire lead, if the pressure sensor is connected to the IMD through a lead, or wirelessly, e.g. through a signal received by communication module 444 of pressure sensor 114.

The pressure sensor, e.g. pressure sensor 114, measures a cardiovascular pressure signal (704). The raw cardiovascular pressure signal measured by the pressure sensor may be stored internally within the pressure sensor, e.g. in memory 446 of pressure sensor 114, for later analysis. As the pressure measures the cardiovascular pressure signal, the IMD may measure the depolarization signal of the heart. In some examples, the pressure sensor may transmit, e.g. via communication module 444 of pressure sensor 114, the unprocessed data to an external location, such as external programmer 104 or IMD 102, for analysis. The pressure sensor may, in some examples, be located within the pulmonary artery of the patient's heart. In other examples, the pressure sensor may be located in other arteries of the cardiovascular system, the aorta, or a ventricle, e.g., the right ventricle.

The pressure sensor, in some examples, determines a plurality of cardiovascular pressure metrics based on the measured cardiovascular pressure signal, including at least one metric indicative of the timing of a cardiovascular pulse (706). The pressure sensor, e.g. pressure sensor 114, analyzes, e.g. via analysis module 442 of pressure sensor 114, the measured cardiovascular signal to determine the cardiovascular pressure metrics, which may include a cardiac pulse interval or rate. Example representative cardiovascular metrics include the cardiac pulse rate, interval or cycle length, systolic pressure, or diastolic pressure. As pressure sensor determines the cardiovascular pressure metric indicative of cardiac pulse timing, e.g., pulse interval, cycle length, or rate, the IMD may determine a corresponding depolarization timing metric based on the depolarization signal, e.g., a depolarization interval, cycle length, or rate.

In some examples, detecting a cardiac pulse allows the pressure sensor, IMD, or an external programmer, e.g. programmer 104, to perform a beat-to-beat comparison of the measured cardiovascular pressure signal, representative cardiovascular pressure metrics and any depolarization data or metric collected by other sensors, e.g. by electrodes 328. However, to avoid power consumption and complexity that may be associated with a beat-to-beat comparison, the pressure sensor may determine a cardiovascular pressure metric indicative of pulse timing. This allows the system to determine and verify the representative cardiovascular metrics over a longer period, limiting the number of communication exchanges with an IMD or external programmer.

In some examples, the pressure sensor transmits the cardiovascular pressure metrics to the IMD (708). This communication may occur over a lead, in examples where the pressure sensor is connected to the IMD via a lead. In many examples, it is beneficial for the patient's health that the number of leads is minimized and communication between the pressure sensor and the IMD may take place wirelessly. In either example, the pressure sensor may use a communication module, e.g. communication module 444 of pressure sensor 114, to control communications.

In some examples, the pressure sensor may transmit the unprocessed cardiovascular signal measured by the pressure sensor to the IMD or an external programmer for further processing. However, such data transmission may be undesired in terms of power consumption, and in some examples the pressure sensor may transmit only the determined cardiovascular pressure metrics to the IMD for further use. The transmission link aboard the pressure sensor may also serve to receive commands from the IMD, such as a wake or sleep command. Data or representative metrics measured by the IMD may be transmitted to the pressure sensor for further processing. Upon receipt of the cardiovascular pressure metrics, the IMD or other device may compare the cardiovascular metric indicative of cardiac pulse timing with the corresponding depolarization timing metric to determine if there is substantial agreement between the two metrics. In situations where the two metrics do not agree, a re-measurement signal may be transmitted to the pressure sensor (710).

The pressure sensor re-measures the cardiovascular pressure signal in response to discarding the at least one representative cardiovascular metric (704). The pressure sensor may be required to discard the detected representative cardiovascular metrics and any stored cardiovascular pressure signal if the metrics and signal are determined to be corrupted, e.g. by noise within the cardiovascular pressure signal. This determination may be made, in some examples, aboard the IMD, e.g., by processor 32 of IMD 102. The determination is made, for example, by comparing the cardiac pulse rate to a depolarization rate, determined from electrically measured depolarizations of the heart.

If there is not substantial agreement between the cardiovascular metric indicative of cardiac pulse timing and the corresponding depolarization timing metric, the cardiovascular pressure metrics stored aboard the IMD may be discarded and a command may be sent to the pressure sensor ordering a re-measurement. Upon receipt of a re-measurement command, the pressure sensor may discard the cardiovascular data and metrics stored within device memory and repeat the measurement of the cardiovascular pressure signal. The pressure sensor may then re-determine values of the cardiovascular pressure metrics based on the re-measured cardiovascular pressure signal and transmit the new cardiovascular pressure metrics to the IMD.

In other examples, the pressure sensor may make the comparison between, for example, a representative pulse rate and heart rate. The pressure sensor may receive the depolarization rate or interval from the IMD for comparison with the pulse rate or interval determined by the pressure sensor based on the sensed pressure signal. If there is insufficient agreement between the two values, the cardiovascular pressure metrics and raw cardiovascular data stored aboard the pressure sensor may be discarded and a notification may be sent to the IMD indicating that the cardiovascular metric received by the IMD is potentially in error and should be discarded. In other examples, the cardiovascular pressure metrics may not be transmitted by the pressure sensor until after the comparison, and the determination of whether or not to transmit the cardiovascular pressure metrics from the pressure sensor to the IMD may be made based on the results of the comparison.

In other examples, IMD may receive the cardiovascular pressure signal from the pressure sensor and the IMD may determine the cardiovascular pressure metrics as well as substantial agreement. In still other examples, another device, e.g., programmer 104 or a server, may receive the pulse rate/interval and depolarization rate/interval and may makes the comparison between the two sets of metrics and transmit signals to one or both the IMD and pressure sensor ordering re-measurement if there is significant disagreement between the metrics.

In some examples, the pressure sensor may enter a sleep or hibernation state to conserve battery life (712). The pressure sensor may enter a sleep state automatically, for example after completing a set of measurements of the cardiovascular pressure signal, or in response to an external command, e.g., from IMD 304. The sleep state may involve a partial shutdown of one or more components of the pressure sensor as well as inactive components of the processor controlling the pressure sensor e.g. processor 440 of pressure sensor 114. Some components of the pressure sensor may remain active, such as a communication module or a timing circuit, in order to wake the pressure sensor in order to perform another set of measurements.

Figure 8:
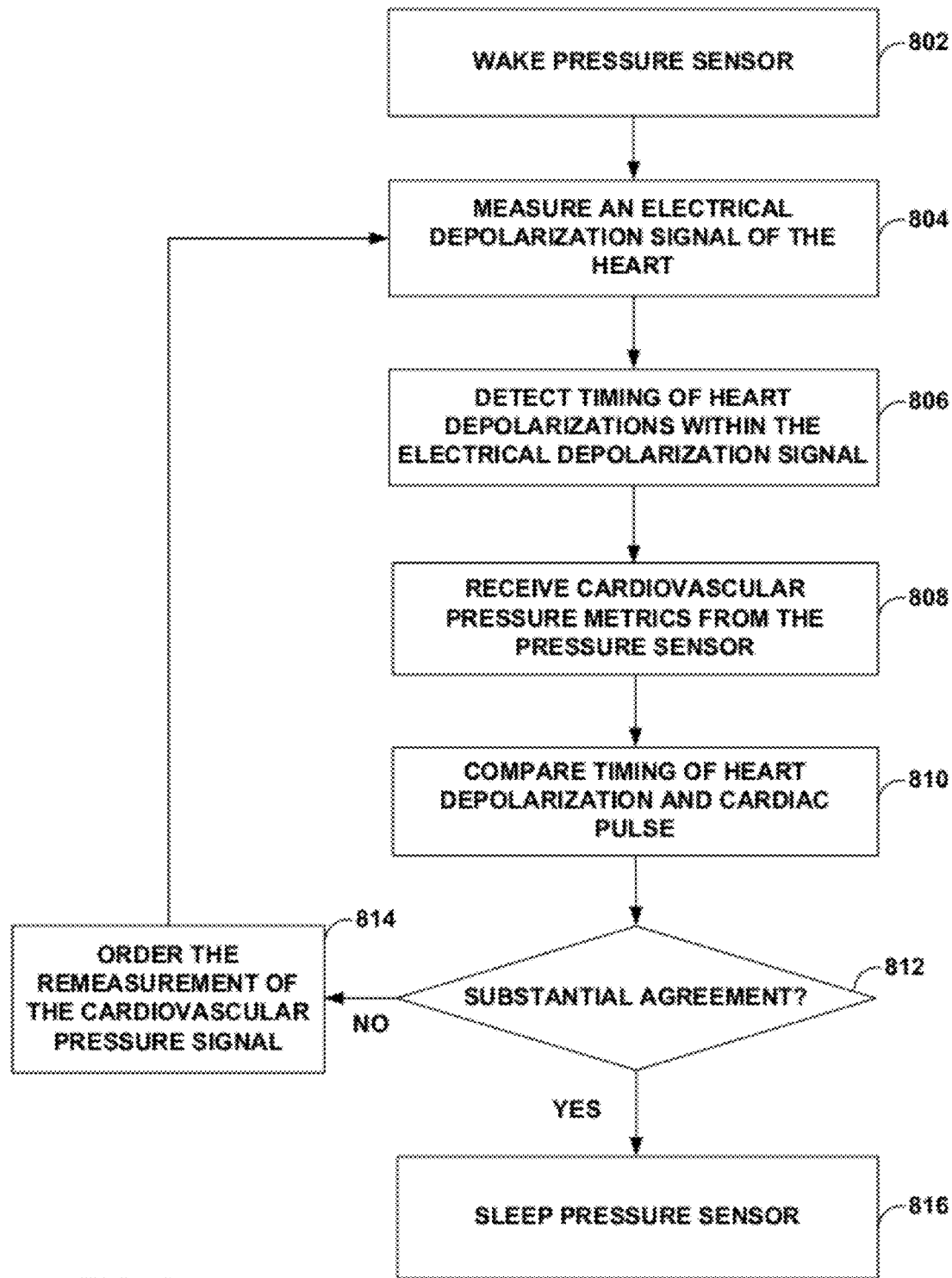
FIG. 8 is a flow diagram illustrating an example method for operating an implantable medical device coupled with a pressure sensor, in accordance with various techniques of this disclosure.

FIG. 8 is a flow diagram illustrating an example method for operating an implantable medical device coupled with a wireless pressure sensor, in accordance with various techniques of this disclosure. Although illustrated and described in the context of an IMD, the method of FIG. 8 may, in other examples, be implemented by an external medical device.

The pressure sensor wakes from a reduced power consumption state, e.g., in response to a command from the IMD (802). The IMD measures an electrical depolarization signal of the heart (804). The IMD detects the timing of one or more heart depolarizations within the electrical depolarization signal (806). The IMD receives at least one representative cardiovascular pressure metric from the pressure sensor, including metric indicative of cardiovascular pulse timing (808). The IMD compares the cardiac pulse and depolarization timings pulse (810), and determines whether there is substantial agreement between the timings (812). If there is not substantial agreement, the IMD orders the re-measurement of the cardiovascular pressure signal (814). If there is substantial agreement between the timings, e.g., between the intervals, cycle lengths, or rates, the pressure sensor returns to a reduced power state once the measurement and re-measurement (if any) procedures complete (816).

In some examples, the IMD, e.g. IMD 102, and pressure sensor, e.g. pressure sensor 114, may spend some or most of its life span in a reduced power consumption sleep or hibernating state. This allows the IMD or pressure sensor to maximize its battery life. The IMD must wake periodically from the sleep state (802). Waking may occur automatically on a fixed schedule, e.g. at certain times of the day, or in response to an external command, e.g. from linked programmer 104. Upon waking, the IMD may transmit a wake command to the pressure sensor. Such a wake command may occur over a wire lead, if the pressure sensor is connected to the IMD through a lead, or wirelessly, e.g. through a signal received by communication module 444 of pressure sensor 114.

The IMD measures a depolarization signal of the heart (804). IMD 102 may measure the depolarization signal through two or more electrodes 328 connected to sensing module 326 of IMD 102. The measured depolarization signal may be stored in memory aboard the IMD, e.g. in memory 322 of IMD 102, for later analysis by the IMD or an external programmer, such as programmer 104. In some examples, the IMD may be implanted subcutaneously. As the IMD measures the depolarization signal, the pressure sensor may measure the corresponding (e.g., corresponding in time) cardiovascular pressure signal to enable a comparison or verification of the two signals.

The IMD detects the timing of one or more depolarizations within the electrical depolarization signal (806). The IMD analyzes, e.g. via analysis module 330 of IMD 102, the electrical signal measured by the IMD. The IMD detects depolarizations within the signal. The IMD determines a metric indicative of depolarization timing, such as an interval between depolarizations, e.g., a cycle length, or rate of depolarizations. The depolarization timing metric may be an average of such values, such as an average of a number of consecutive intervals or an average rate during a plurality of cardiac cycles.

The IMD also receives at least one cardiovascular pressure metric indicative of cardiac pulse timing from the pressure sensor (808). A cardiovascular pressure metric indicative of cardiac pulse timing may include one or more of an interval between cardiac pulses, e.g., a cardiac cycle length, or a pulse rate. The cardiovascular pressure metric indicative of cardiac pulse timing may, in some examples, be an average of several such values, such as an average cycle length or pulse rate over several cardiac cycles. The IMD may receive the cardiovascular pressure metric either over a lead, provided the pressure sensor is connected to IMD via a lead, or wirelessly, e.g., via communication module 328 of IMD 102. The IMD may store the cardiovascular pressure metric in memory, e.g. in memory 322 of IMD 102.

In some examples, the IMD may receive unprocessed cardiovascular pressure data from the pressure sensor. In such examples, the IMD may process the cardiovascular pressure signal to determine cardiovascular pressure metrics. The cardiovascular pressure signal may be stored in memory on IMD.

The IMD compares the timing of the heart depolarization and the cardiac pulse, e.g., via processor 320 (810). The IMD orders the re-measurement of the cardiovascular pressure signal if the electrical depolarization and cardiac pulse timing do not substantially agree (814). This command may, in some examples, be sent when the heart (depolarization) rate and cardiac pulse rate do not agree. The IMD may also discard any other cardiovascular pressure metrics, e.g., systolic or diastolic pressures, stored in local memory that correspond to the failed comparison, e.g., are based on the same sampling of the cardiovascular pressure signal. In some examples, the pressure sensor may enter a sleep or hibernation state to conserve battery life, e.g., upon substantial agreement of the timing metrics such that the cardiovascular pressure metrics are accepted and no further measurement is required (816).

Figure 9:
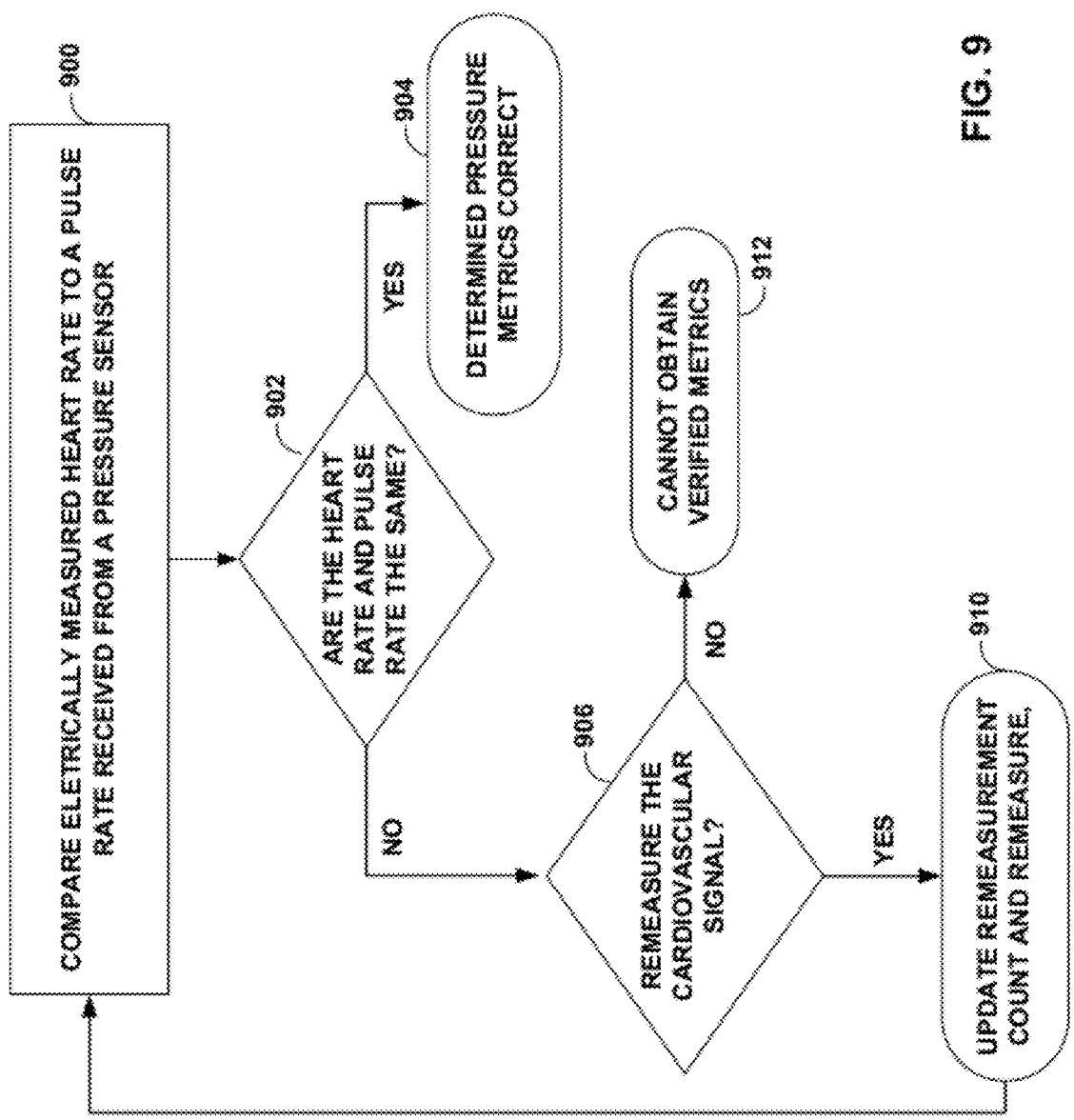
FIG. 9 is a decision tree describing an example comparison of a pulse rate and a heart rate, in accordance with various techniques of this disclosure.

FIG. 9 is a decision tree describing an example comparison of a pulse (pressure) rate and a heart (depolarization) rate in accordance with various techniques of this disclosure. Although the decision tree of FIG. 9 illustrates an example in which with rates are compared, in other examples intervals, cycle lengths, or other metrics representative of the timing of depolarizations and pulses may be compared.

In the illustrated example, the IMD, pressure sensor, programmer, or another computing device compares the heart rate electrically measured by IMD 102 to a pulse rate received from a pressure sensor (900). The comparison determines whether the heart rate and pulse rate are substantially the same (902). If the heart and pulse rates are substantially the same ("YES" branch of 902), the comparison module determines that other cardiovascular pressure metrics determined based on the cardiovascular signal are reliable (904). The pressure sensor may then enter a sleep mode.

If the heart rate and pulse rate are not substantially the same ("NO" branch of 902), the comparison module determines if it is appropriate to re-measure the cardiovascular pressure signal (906). If the re-measurement is appropriate, a re-measurement counter may be updated, a command may be sent to the pressure sensor to conduct a re-measurement of the cardiovascular signal, and the process may repeat from step 900 (910). If re-measurement is not appropriate, the IMD or other device may determine that the pressure sensor is unable to obtain a verifiable cardiovascular pressure metric (912).

Other processes or algorithms which would use the cardiovascular pressure metrics may continue to use previously determined and verified metric values, in some examples.

In some examples, the IMD compares the electrically measured heart rate to a pulse rate received from a pressure sensor (900). The comparison may be made by a processor, e.g. processor 320 of IMD 102. The IMD compares the pulse rate to the heart rate measured over the same time period, e.g., the rates correspond to a common period of time during which the pressure and depolarization signals were sampled.

The verification may include determining whether the heart rate and pulse rate are substantially the same (902). The agreement between the two rates may not need to be exact. In some examples, the agreement between the rates may be within a threshold value of each other to compensate for minor or anticipated differences in the identification of depolarizations and pulses by the IMD and pressure sensor. The threshold value may be a default value, or a user selectable or programmable value, which may thereby be patient-specific. In some examples, a patient-specific threshold may be automatically determined by the IMD or another device described herein. For example, the IMD or device may monitor depolarization and pulse rates during a threshold determination period to identify normal variances in the rates, and set the threshold accordingly. The threshold determination period may occur shortly after implantation of one or both of the IMD and pressure sensor, during a follow-up visit, or periodically. In some examples, the threshold may dynamically adjust as a function of one or both of the pulse or depolarization intervals. In any case, if the heart rate and the cardiac pulse rate agree, the determined pressure metrics may be verified as reliable (904).

If the heart rate and cardiac pulse rate do not agree, the IMD may determine if the cardiovascular pressure signal should be re-measured (906). In order to conserve battery power, the pressure sensor and/or IMD may maintain a count of the number of re-measurements of the cardiovascular pressure signal. If the number of re-measurements of the cardiovascular pressure signal exceeds a predetermined threshold, the IMD or pressure sensor may elect to simply end the re-measurement cycle and conserve power for other activities. If the predefined threshold has not been exceeded, the IMD may update the re-measurement count, signal the pressure sensor to re-measure the cardiovascular pressure signal, and repeat the verification process from comparison step 900 (910). In some examples, the re-measurement may be delayed for a set period, e.g., in order to allow a noise generating condition affecting the cardiovascular pressure signal to dissipate.

If the IMD or pressure sensor determines that re-measurement of the cardiovascular signal is inappropriate, the system may determine that it cannot obtain verified cardiovascular pressure metrics (912). The IMD and pressure sensor may take a variety of actions, including generating an alert, e.g., communicating with an external device to generate an alert message for the patient or health care provider, or waiting for another scheduled measurement cycle. Continuous disagreement between the heart rate and cardiac pulse rate (or electrical depolarization and cardiac pulse) may indicate a problem within the system, such as fracture of a lead carrying an electrode used to detect the electrical depolarizations of the heart. The disagreement may also indicate that the sensing threshold parameters of the IMD or the pressure sensor require adjustment, or that there is a cardiac event, e.g., tachyarrhythmia, underway.

The previous examples included techniques for verifying the reliability of pressure metrics based on a comparison of a pressure metric indicative of the timing of cardiac pulses, e.g., the rate of pulses in the pressure waveform, with the timing of cardiac depolarizations, e.g., the heart rate determined based on one or more intervals between consecutively detected R-waves. In some examples, pressure metrics may be verified based on a comparison of two cardiovascular signals from two pressure sensors. For example, first pressure metrics determined based on a first cardiovascular pressure signal sensed by a first pressure sensor at a first location within the patient may be verified based on a comparison with a second pressure metric determined based on a second cardiovascular pressure signal sensed by a second pressure sensor at a second location within the patient.

The comparison may be between first and second metrics indicative of the timing of cardiac pulses detected within the first and second waveforms. In some examples, the second cardiovascular pressure signal from the second pressure sensor may more reliably include cardiac pulses than the first cardiovascular pressure signal from the second pressure sensor, e.g., due to the location of the pressure sensors. For example, the first pressure sensor may be located outside of the heart of the patient, e.g., within the pulmonary artery or aorta, and the second pressure sensor may be located within the heart of the patient, e.g., within the right ventricle. The various techniques described herein in the context of a comparison of pulse and depolarization timing may be applied to a comparison of pulse timing in first and second cardiovascular pressure waveforms.

Figure 10:
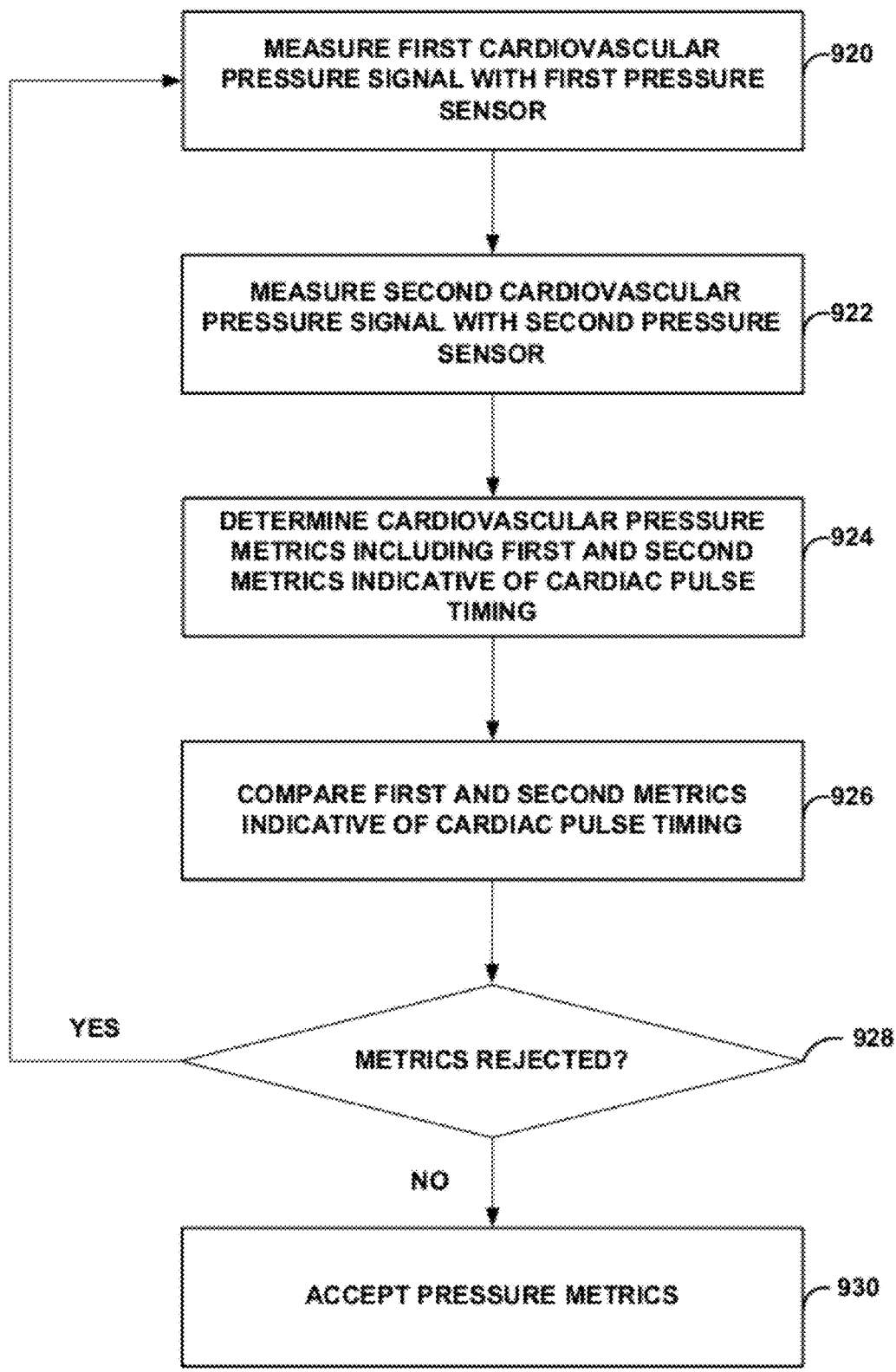
FIG. 10 is a flow diagram illustrating an example technique for verifying cardiovascular pressure metrics based on a comparison signals from two pressure sensors.

FIG. 10 is a flow diagram illustrating an example technique for verifying cardiovascular pressure metrics based on a comparison signals from two pressure sensors. According to the example of FIG. 10, a first implanted pressure sensor measures a first cardiovascular pressure signal (920). During the same time period, e.g., at the same time, a second implanted pressure sensor measures a second cardiovascular pressure signal (922).

The first pressure sensor, the second pressure sensor, and/or one or more other devices determines a first plurality of cardiovascular pressure metrics based on the first signal and at least one second cardiovascular pressure metrics based on the second signal (924). One of the first cardiovascular pressure metrics is indicative of cardiac pulse timing, e.g., is a first cardiac pulse rate. The second cardiovascular pressure metrics is also indicative of cardiac pulse timing, e.g., is a second cardiac pulse rate.

The first pressure sensor, the second pressure sensor, and/or one or more other devices compares the first and second metrics indicative of cardiac pulse timing (926). If there is not substantial agreement between the first and second pressure metrics indicative of timing (NO branch of 928), e.g., according to the techniques described herein with respect to a pressure/depolarization comparison, the plurality of first pressure metrics are rejected by the one or more sensors or other devices. In some examples, additional second pressure metrics determined based on the second cardiovascular signal may also be rejected. In response to the rejection, the first and second pressure sensors may re-measure the first and second pressure signals, e.g., autonomously or in response to a command (920). If there is substantial agreement between the first and second pressure metrics indicative of timing (YES branch of 928), e.g., according to the techniques described herein with respect to a pressure/depolarization comparison, the plurality of first pressure metrics are accepted by the one or more sensors or other devices, e.g., may be stored, presented to a user, or used to determine treatment of the patient.

Figure 11:
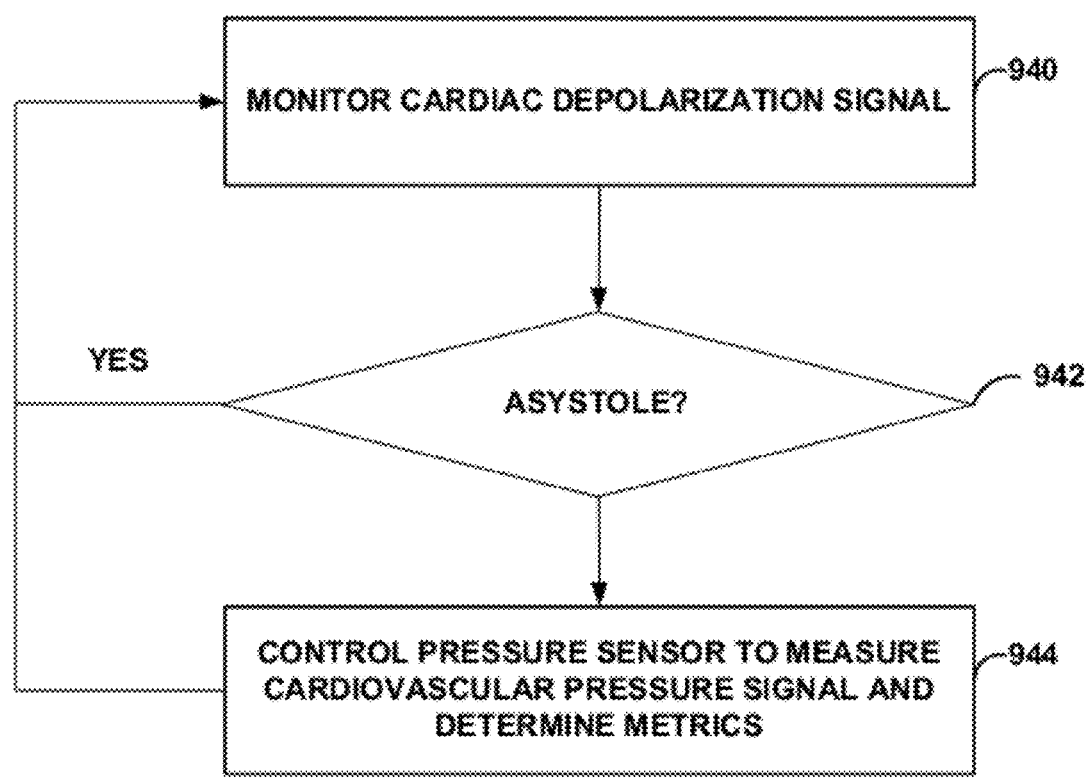
FIG. 11 is a flow diagram illustrating an example method that may be implemented by an IMD, or other device, to determine when to control a pressure sensor to measure a cardiovascular pressure signal and determine cardiovascular pressure metrics.

FIG. 11 is a flow diagram illustrating an example method that may be implemented by an IMD, or other device, to determine when to control a pressure sensor to measure a cardiovascular pressure signal and determine cardiovascular pressure metrics. The example method of FIG. 11 is described, for purposes of illustration, as being performed by in IMD. According to the example method, the IMD controls the pressure measurement in response to detection of a particular heart rate condition—asystole.

According to the example method of FIG. 11, the IMD monitors a cardiac depolarization signal, e.g., to detect R-waves and determine a heart rate, as described herein (940). The IMD determines whether asystole is detected (942). For example, the IMD may detect asystole based on a threshold period of time passing, such as three seconds, without detecting a cardiac depolarization, e.g., R-wave. If asystole is not detected (NO branch of 942), the IMD continues to monitor the cardiac depolarization signal. If asystole is detected (YES branch of 942), the IMD controls the pressure sensor to measure a cardiovascular pressure signal and determine one or more cardiovascular pressure metrics based on the pressure signal (944). The IMD, or another device, may use the pressure metrics to confirm the asystole, e.g., determine whether there is truly an absence of depolarizations or whether the IMD did not sense depolarizations that occurred. The determination may be based on the presence or absence of cardiac pulses in the pressure signal. Modification of depolarization sensing, storage of an episode (which may include the depolarization and pressure waveforms, or delivery of a therapy, e.g., pacing, cardioversion, or defibrillation, may be performed by one or more devices based on the one or more pressure metrics confirming or denying the detected asystole.

Figure 12:
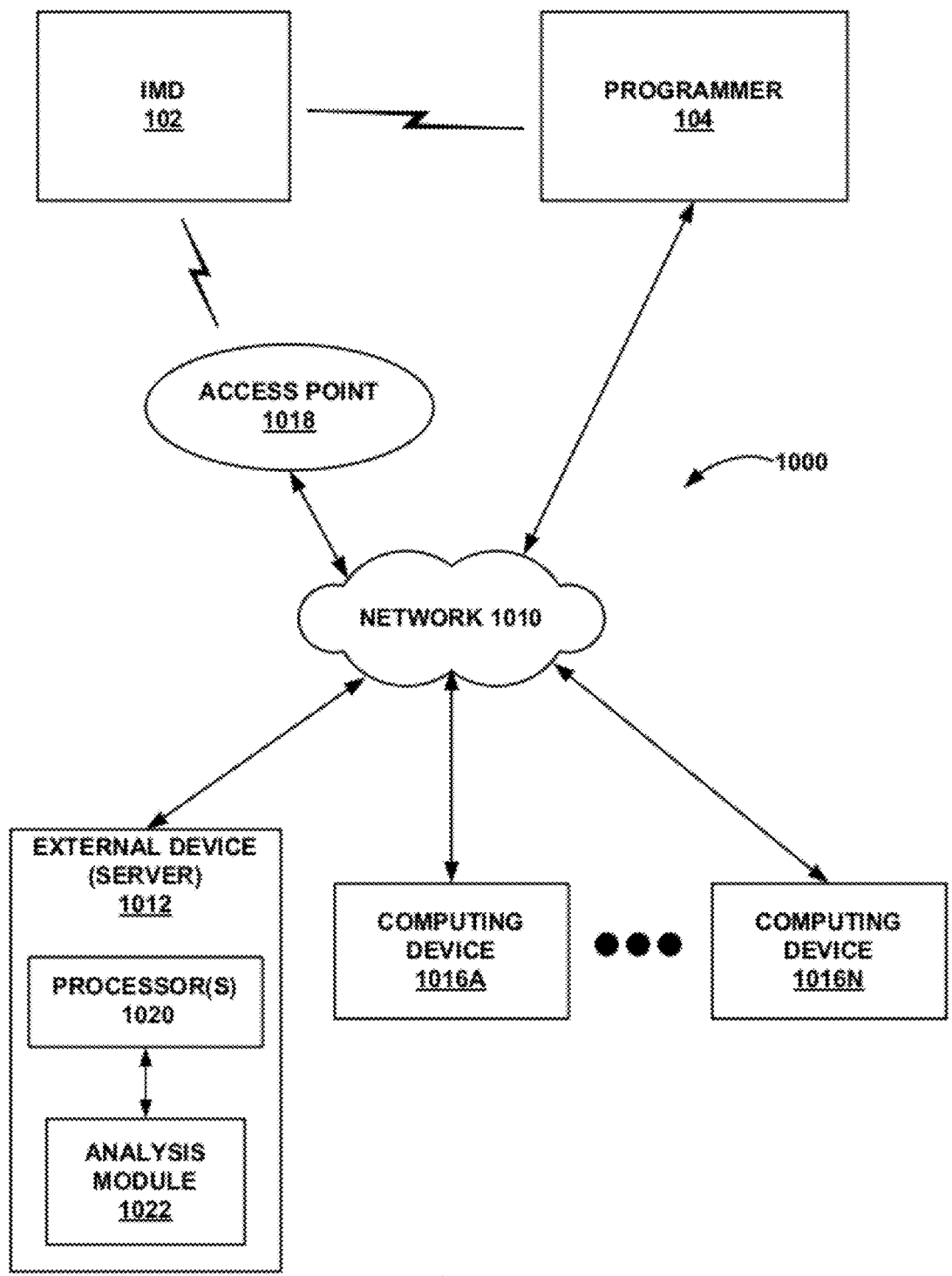
FIG. 12 is a block diagram illustrating an example system that includes a server and one or more computing devices that are coupled to an IMD and a programmer.

FIG. 12 is a block diagram illustrating an example system 1000 that includes an external device, such as a server 1012, and one or more computing devices 1016A-1016N, that are coupled to the IMD 102 and programmer 104 via a network 1010. In this example, IMD 102 may use a communication module, e.g. communication module 328, to communicate with programmer 104 via a first wireless connection, and to communication with an access point 1018 via a second wireless connection. In the example of FIG. 12, access point 1018, programmer 104, server 1012, and computing devices 1016A-1016N are interconnected, and able to communicate with each other, through network 1010. In some cases, one or more of access point 1018, programmer 104, server 1012, and computing devices 1016A-1016N may be coupled to network 1010 through one or more wireless connections. IMD 102, programmer 104, server 1012, and computing devices 1016A-1016N may each comprise one or more processors, such as one or more microprocessors, DSPs, ASICs, FPGAs, programmable logic circuitry, or the like, that may perform various functions and operations, such as those described herein.

Access point 1018 may comprise a device that connects to network 1010 via any of a variety of connections, such as telephone dial-up, digital subscriber line (DSL), or cable modem connections. In other examples, access point 1018 may be coupled to network 1010 through different forms of connections, including wired or wireless connections. In some examples, access point 1018 may be co-located with the patient, e.g. patient 10, and may comprise one or more programming units and/or computing devices (e.g., one or more monitoring units) that may perform various functions and operations described herein. For example, access point 1018 may include a home-monitoring unit that is co-located with the patient and that may monitor the activity of IMD 102.

In some cases, server 1012 may be configured to provide a secure storage site for data that has been collected from IMD 102 and/or programmer 104. Network 1010 may comprise a local area network, wide area network, or global network, such as the Internet. In some cases, programmer 104 or server 1012 may assemble data in web pages or other documents for viewing by trained professionals, such as clinicians, via viewing terminals associated with computing devices 1016A-1016N. The illustrated system of FIG. 10 may be implemented, in some aspects, with general network technology and functionality similar to that provided by the Medtronic CareLink® Network developed by Medtronic, Inc., of Minneapolis, Minn.

In some examples, processor 1020 of server 1012 may be configured to receive pressure information from a pressure sensor(s), e.g., pressure sensor 114, and/or depolarization information from an IMD, e.g., IMD 102, for processing by analysis module 1022 in the manner described throughout this disclosure. Analysis module 1022 may determine cycle lengths, rates, systolic pressures, and/or diastolic pressures based on the received information using any of the techniques described in this disclosure. Processor 1020 may compare rate, cycle lengths, or any other metrics indicative of the timing of depolarizations and pulses, using any of the techniques described herein, in order to verify the reliability of one or more cardiovascular pressure metrics.

Processor 1020 may provide alerts to users, e.g., to the patient via access point 1018 or to a clinician via one of computing devices 1016, identifying change, e.g., worsening, in patient condition based on cardiac cycle length and/or pressure metrics measured from pulmonary arterial pressures. Processor 1020 may suggest to a clinician, e.g., via programmer 104 or a computing device 1016, a change in a therapy, such as CRT, based on cardiac cycle length and/or pressure metrics measured from pulmonary arterial pressures. Processor 1020 may also adjust or control the delivery of therapy by IMD 102, e.g., electrical stimulation therapy and/or a therapeutic substance, via network 1010.

In some examples, using the various techniques described above, cardiovascular pressure metrics obtained from a remotely located pressure sensor may be verified based on a measured electrical depolarization signal of the heart without requiring additional leads implanted into the patient. The cardiovascular pressure measurements and verification may be periodic, e.g., hourly or daily. In some examples, the compared depolarization and pulse timing metrics may be averages over a number of cardiac cycles, e.g., average pulse and depolarization rates.

In some examples, the IMD may perform a beat-to-beat verification of the pressure metrics transmitted by the pressure sensor. The beat-to-beat verification may be performed periodically for a period of time, or continuously. The beat-to-beat verification may be a beat-to-beat comparison of average timing metrics, or may include verifying that an individual detected electrical depolarization of the heart occurred at about the same time as, or with an expected timing correlation to, the detected cardiovascular pulse. In the latter examples, the IMD or other device may verify that each electric depolarization corresponds to a cardiac pulse, and vice versa, to ensure that the pressure sensor is not over or under sensing the cardiovascular pressure fluctuations.

In some configurations, the pressure sensor may be activated by the IMD in response to electrically detected cardiac events, such as an arrhythmia. Cardiovascular pressure metrics provided in response to such an activation may verify the detection of arrhythmia by the IMD, or provide useful information for diagnosing a condition underlying the arrhythmia. In some examples, the pressure sensor and the IMD may be used in conjunction to provide a more rapid and accurate diagnosis of specific cardiac events, such as a premature ventricular contraction (PVC).

Furthermore, in some examples, the IMD may prompt the pressure sensor to delay a periodic, e.g., daily, measurement of cardiovascular pressure. For example, the IMD may prompt the pressure sensor to delay the measurement in response to detecting a depolarization rate at which the corresponding cardiac contraction rate would be such that cardiovascular pressure metrics would be unreliable.

Various example implementations of the disclosure have been described. These and other example implementations are within the scope of the following claims.

The invention claimed is:

1. A system comprising:
   at least one pressure sensor configured to measure a cardiovascular pressure signal;
   a medical device configured to measure an electrical depolarization signal of the heart;
   at least one analysis module configured to:
      determine a plurality of cardiovascular pressure metrics based on the measured cardiovascular pressure signal, wherein the plurality of cardiovascular pressure metrics includes at least one cardiovascular pressure metric indicative of a timing of at least one cardiac pulse, and at least one of a systolic pressure and a diastolic pressure; and
      determine a cardiac electrical metric indicative of a timing of at least one heart depolarization based on the measured electrical depolarization signal; and
   at least one processor configured to:
      compare the timing of the at least one cardiac pulse to the timing of the at least one heart depolarization; and
      determine whether to discard the plurality of cardiovascular pressure metrics based on whether the timing of the at least one cardiac pulse and the timing of the at least one heart depolarization substantially agree.

2. The system of claim 1, wherein the cardiac electrical metric indicative of the timing of at the least one heart depolarization comprises a heart rate and the at least one cardiovascular pressure metric indicative of the timing of the at least one cardiac pulse comprises a pulse rate.

3. The system of claim 1, wherein the at least one pressure sensor is wirelessly coupled to the medical device.

4. The system of claim 3, wherein the pressure sensor is configured to wirelessly transmit the plurality of cardiovascular metrics to the medical device.

5. The system of claim 1, wherein the processor is configured to control the at least one pressure sensor to re-measure the cardiovascular pressure signal if the plurality of cardiovascular pressure metrics is discarded.

6. The system of claim 5, wherein the processor is configured to:
   determine a number of times that the cardiovascular pressure signal has been re-measured in response to discarding the plurality of cardiovascular pressure metrics;
   compare the number of times that the cardiovascular pressure signal has been re-measured to a predetermined threshold; and
   determine whether to control the at least one pressure sensor to re-measure the cardiovascular pressure signal based on the comparison.

7. The system of claim 1, wherein the medical device comprises the processor.

8. The system of claim 1, wherein the medical device is configured for subcutaneous implantation within a patient.

9. A system comprising:
   means for measuring a cardiovascular pressure signal;
   means for measuring an electrical depolarization signal of the heart;
   means for determining a plurality of cardiovascular pressure metrics based on the measured cardiovascular pressure signal, wherein the plurality of cardiovascular pressure metrics includes at least one cardiovascular pressure metric indicative of a timing of at least one cardiac pulse, and at least one of a systolic pressure and a diastolic pressure;
   means for determining a cardiac electrical metric indicative of a timing of at least one heart depolarization within the measured electrical depolarization signal;
   means for comparing the timing of the at least one cardiac pulse to the timing of the at least one heart depolarization ; and
   means for determining whether to discard the plurality of cardiovascular pressure metrics based on whether the timing of the at least one cardiac pulse and the timing of the at least one heart depolarization substantially agree.

10. The system of claim 9, wherein the cardiac electrical metric indicative of the timing of the at least one heart depolarization comprises a heart rate and the at least one cardiovascular pressure metric indicative of the timing of the at least one cardiac pulse comprises a pulse rate.

* * * * *